(12) United States Patent
Hendrich et al.

(10) Patent No.: US 10,274,441 B2
(45) Date of Patent: Apr. 30, 2019

(54) GENERATING AN IMAGE OF AN OBJECT OR A REPRESENTATION OF DATA ABOUT THE OBJECT

(71) Applicant: Carl Zeiss Microscopy GmbH, Jena (DE)

(72) Inventors: Christian Hendrich, Westhausen (DE); Bernd Schindler, Aalen (DE)

(73) Assignee: CARL ZEISS MICROSCOPY GMBH, Jena (DE)

( * ) Notice: Subject to any disclaimer, the term of this patent is extended or adjusted under 35 U.S.C. 154(b) by 64 days.

(21) Appl. No.: 15/600,910

(22) Filed: May 22, 2017

(65) Prior Publication Data

US 2017/0336335 A1   Nov. 23, 2017

(30) Foreign Application Priority Data

May 20, 2016   (DE) .................. 10 2016 208 689

(51) Int. Cl.
*G01N 23/2251* (2018.01)
*H01J 37/22* (2006.01)
(Continued)

(52) U.S. Cl.
CPC ........ *G01N 23/2251* (2013.01); *H01J 37/222* (2013.01); *H01J 37/263* (2013.01);
(Continued)

(58) Field of Classification Search
CPC .. H01J 37/00; H01J 37/02; H01J 37/04; H01J 37/07; H01J 37/153; H01J 37/26; H01J 37/261; H01J 37/263
(Continued)

(56) References Cited

U.S. PATENT DOCUMENTS 7,838,832 B1   11/2010   Mankos et al.
8,779,357 B1 *   7/2014   Miller .................. H01J 37/222
                                                              250/306

(Continued)

FOREIGN PATENT DOCUMENTS

EP          1 388 883 B1       6/2013
WO     WO 02/067286 A2        8/2002

OTHER PUBLICATIONS

L. Reimer, "Image Formation in Low Voltage Scanning Microscopy", SPIE 1993, p. 102.

(Continued)

*Primary Examiner* — Jason L McCormack
(74) *Attorney, Agent, or Firm* — Muirhead and Saturnelli, LLC

(57) ABSTRACT

Generating an image of an object and/or a representation of data about the object uses a particle beam apparatus. The particle beam apparatus comprises at least one control unit for setting a guide unit by selecting a value of a control parameter of the control unit. A functional relationship is determined between a first control parameter value and a second control parameter value depending on the predeterminable range of a landing energy of the particles. A desired value of the landing energy is set. The value of the control parameter corresponding to the desired value of the landing energy is selected on the basis of the determined functional relationship and the guide unit is controlled using the value of the control parameter corresponding to the desired value of the landing energy.

15 Claims, 10 Drawing Sheets

(51) Int. Cl.
    *H01J 37/28*     (2006.01)
    *H01J 37/26*     (2006.01)
    *G01N 23/04*     (2018.01)

(52) U.S. Cl.
    CPC ............ *H01J 37/265* (2013.01); *H01J 37/28* (2013.01); *G01N 23/04* (2013.01); *H01J 2237/2813* (2013.01)

(58) Field of Classification Search
    USPC .......................................... 250/306, 307, 311
    See application file for complete search history.

(56) References Cited

U.S. PATENT DOCUMENTS

| | | |
|---|---|---|
| 2004/0036031 A1 | 2/2004 | Rose et al. |
| 2009/0256076 A1* | 10/2009 | Fukuda ................ H01J 37/145 250/311 |
| 2011/0187847 A1 | 8/2011 | Bai et al. |
| 2013/0037714 A1 | 2/2013 | Boughorbel et al. |
| 2016/0013015 A1 | 1/2016 | Potocek et al. |

OTHER PUBLICATIONS

L. Reimer, "Physics of Image Formation and Microanalysis", in Scanning Electron Microscopy, Emission of Electrons and X-Ray Quanta, 1985, pp. 136 f.

"Signal Manipulation" Display and record system.

Albert Rose, (physicist), Text and Image Sources, Contributors, and Licenses, Wikipedia.

L. Frank, et al., "Strategies for low- and very-low-energy SEM", Japanese Society of Electron Microscopy, Journey of Electron Microscopy 48(3): 205-219, 1999.

\* cited by examiner

GENERATING AN IMAGE OF AN OBJECT OR A REPRESENTATION OF DATA ABOUT THE OBJECT

TECHNICAL FIELD

The system described herein relates to a generating an image of an object and/or a representation of data about the object using a particle beam apparatus, such as an electron beam apparatus or as an ion beam apparatus.

BACKGROUND

Electron beam apparatuses, in particular a scanning electron microscope (also referred to as SEM below) and/or a transmission electron microscope (also referred to as TEM below), are used to examine objects (also referred to as samples) in order to obtain knowledge in respect of the properties and behavior of the objects under certain conditions. In an SEM, an electron beam (also referred to as primary electron beam below) is generated by means of a beam generator and focused on an object to be examined by way of a beam guiding system. An objective lens is used for focusing purposes. The primary electron beam is guided over a surface of the object to be examined by way of a deflection device. This is also referred to as scanning. The area scanned by the primary electron beam is also referred to as scanning region. Here, the electrons of the primary electron beam interact with the object to be examined. Interaction particles and/or interaction radiation result as a consequence of the interaction. By way of example, the interaction particles are electrons. In particular, electrons are emitted by the object—the so-called secondary electrons—and electrons of the primary electron beam are scattered back—the so-called backscattered electrons. The interaction particles form the so-called secondary particle beam and are detected by at least one particle detector. The particle detector generates detection signals which are used to generate an image of the object. An imaging of the object to be examined is thus obtained. By way of example, the interaction radiation is x-ray radiation or cathodoluminescence. At least one radiation detector is used to detect the interaction radiation.

In the case of a TEM, a primary electron beam is likewise generated by means of a beam generator and directed onto an object to be examined by means of a beam guiding system. The primary electron beam passes through the object to be examined. When the primary electron beam passes through the object to be examined, the electrons of the primary electron beam interact with the material of the object to be examined. The electrons passing through the object to be examined are imaged onto a luminescent screen or onto a detector—for example in the form of a camera—by a system comprising an objective. By way of example, the aforementioned system additionally also comprises a projection lens. Here, imaging may also take place in the scanning mode of a TEM. As a rule, such a TEM is referred to as STEM. Additionally, provision may be made for detecting electrons scattered back at the object to be examined and/or secondary electrons emitted by the object to be examined by means of at least one further detector in order to image the object to be examined.

Combining the function of an STEM and an SEM in a single particle beam apparatus is known. It is therefore possible to carry out examinations of objects with an SEM function and/or with an STEM function using this particle beam apparatus.

Moreover, a particle beam apparatus in the form of an ion beam column is known. Ions used for processing an object are generated by means of an ion beam generator arranged in the ion beam column. By way of example, material of the object is ablated or material is applied onto the object during the processing. The ions are additionally or alternatively used for imaging.

Furthermore, the prior art has disclosed the practice of analyzing and/or processing an object in a particle beam apparatus using, on the one hand, electrons and, on the other hand, ions. By way of example, an electron beam column having the function of an SEM is arranged at the particle beam apparatus. Additionally, an ion beam column, which was already explained above, is arranged at the particle beam apparatus. The electron beam column with the SEM function serves, in particular, for examining further the processed or unprocessed object, but also for processing the object.

An object may be imaged with a high spatial resolution using an electron beam apparatus. In particular, this is achieved by a very small diameter of the primary electron beam in the plane of the object. Further, the spatial resolution may improve the higher the electrons of the primary electron beam are initially accelerated in the electron beam apparatus and decelerated to a desired energy (referred to as landing energy) at the end of the objective lens or in the region of the objective lens and the object. By way of example, the electrons of the primary electron beam are accelerated using an acceleration voltage of 2 kV to 30 kV and guided through an electron column of the electron beam apparatus. The electrons of the primary electron beam are only decelerated to the desired landing energy, with which they are incident on the object, in the region between the objective lens and the object. By way of example, the landing energy of the electrons in the primary electron beam lies in the range between 10 eV and 30 keV.

There are objects which, on account of their structure, may only be expediently examined in an electron beam apparatus if the electrons in the primary electron beam incident on these objects only have a low landing energy, for example an energy of less than 100 eV. Electrons with such low energy for example ensure that these specific objects are not destroyed and/or do not charge upon irradiation by electrons. Further, electrons at such low energies are particularly suitable for obtaining an image with a high surface sensitivity (i.e. a particularly good information content in respect of the topography and/or the material of the surface of the object) of an object to be examined.

When generating an image of the object, the user of an electron beam apparatus is always prudent to obtain the ideal image quality of an image of the object which is required for examining an object. Expressed differently, a user always wishes to create an image of the object with such a high image quality that they are able to analyze the object to be examined well on account of the image and the image information contained therein. Here, the image quality may be determined by means of e.g. objective criteria. By way of example, the image quality of an image becomes better with increasing resolution in the image or with increasing contrast. Alternatively, the image quality may be determined on the basis of subjective criteria. Here, a user determines individually as to whether or not an obtained image quality is sufficient. However, what may by all means occur in this case is that the image quality deemed sufficient by a first user is not considered sufficient by a second user. By way of example, the image quality of an image of an object may also be determined on the basis of the signal-to-noise ratio of the detector signal. The image quality is not sufficiently good in the case of a signal-to-noise ratio in the range from 0 to 5. By way of example, if the signal-to-noise ratio lies in the range from 20 to 40, this is referred to as a good signal-to-noise ratio (and hence also a good and sufficient image quality). The direction of the secondary particle beam may also be a measure for the image quality. The secondary electrons may be emitted from the object at different solid angles. Further, the backscattered electrons may be backscattered into different solid angles at the object. The direction of the secondary particle beam (i.e. the solid angles along which the secondary particle beam extend) may be influenced by tilting the primary electron beam and/or the object in relation to the optical axis of the electron beam apparatus. As a result of this, it is possible, on the one hand, to select the direction of the secondary particle beam in such a way that the secondary particle beam is incident on a desired detector. On the other hand, it is possible to influence both the number of the generated secondary electrons and the number of the back-scattered backscattered electrons by way of the aforementioned tilting. By way of example, if the primary electron beam is incident into the object parallel to a crystal lattice of an object, the number of secondary electrons and/or backscattered electrons reduces. The detection signal becomes weaker. This leads to reduction in the image quality. It is possible to increase the number of secondary electrons and number of backscattered electrons by setting the tilt of the primary electron beam. Using such a setting, it is possible to differentiate crystals with a first orientation from crystals with a second orientation on the basis of the strength of the detection signal.

As mentioned above, it is also possible to detect interaction radiation, for example cathodoluminescence and x-ray radiation. When detecting interaction radiation, a user of an electron beam apparatus may by all means be prudent to obtain the quality of the representation of the detection signals of a radiation detector based on the detected interaction radiation which is required for examining an object. By way of example, if x-ray radiation is detected by the radiation detector, the quality of the representation is determined e.g. by a good detection signal of the radiation detector. By way of example, the latter is embodied as an EDX detector. By way of example, the quality of the representation is then influenced by the count rate of the detected x-ray quanta on the one hand and, on the other hand, by the full width at half maximum of the measured peaks in the x-ray spectrum. The quality of the representation of the detection signals increases with higher count rate and smaller full width at half maximum. By way of example, if cathodoluminescence is detected by a radiation detector, the quality of the representation may likewise be determined e.g. by a good detection signal of the radiation detector. By way of example, the quality of the representation is determined by the count rate of the detected photons of the cathodoluminescence. The count rate may be influenced by a suitable optical unit for light. Further, the primary electron beam may be set in such a way that the object emits as many photons as possible overall or as many photons as possible within a specific wavelength interval.

As a rule, in order to obtain a good image quality of an image and/or a good representation of the detection signals based on the detected interaction radiation, which image and/or representation is/are generated by means of an electron beam apparatus, a user of an electron beam apparatus known from the prior art initially selects a desired landing energy with which the electrons are incident on the object. Following this, the user selects settings of further control parameters of at least one control unit. By way of example, the control parameters are physical variables, in particular a control current or a control voltage, but also e.g. the ratio of physical variables, in particular an amplification of physical variables. The values of the physical variables are adjustable at the control units or using the control units and these control and/or feed the units of the electron beam apparatus in such a way that desired physical effects, for example, the generation of specific magnetic fields and/or electrostatic fields, are brought about.

A first control parameter of a first control unit sets the contrast in the generated image. In principle, the contrast is the brightness difference (i.e. the intensity difference) between the brightest pixel with a maximum luminance $L_{max}$ and the darkest pixel with a minimum luminance $L_{min}$ in an image. A smaller brightness difference between the two pixels means a low contrast. A larger brightness difference between the two pixels means a high contrast. By way of example, the contrast may be specified as Weber contrast or as Michelson contrast. Here, the following applies for the Weber contrast:

$$K_W = \frac{L_{max}}{L_{min}} - 1 \text{ with } 0 \le K_W \le \infty \quad [1]$$

The following applies for the Michelson contrast:

$$K_M = \frac{L_{max} - L_{min}}{L_{max} + L_{min}} \text{ with } 0 \le K_M \le 1 \quad [2]$$

The contrast which is substantially generated by the secondary electrons is determined by the topography of the surface of the object. On the other hand, the contrast which is substantially generated by the backscattered electrons is substantially determined by the material of the imaged object region. It is also referred to as material contrast. The material contrast depends on the mean atomic number of the imaged region of the object. By way of example, the contrast increases when a higher gain factor is set at an amplifier of the detector, wherein the detector is used to detect the secondary electrons and/or backscattered electrons. The amplifier amplifies the detection signal generated by the detector. Analogously, the contrast e.g. decreases when a smaller gain factor is set at the amplifier of the detector.

A second control parameter of a second control unit sets the brightness in the generated image. In principle, the brightness in an image is related to each pixel in the image. A first pixel with a higher brightness value than a second pixel appears brighter in the image than the second pixel. By way of example, the brightness is set by setting a gain factor of the detection signal of the detector. Here, the brightness of each pixel in the image is increased or lowered by an identical amount, for example also using a color table stored in a memory unit, with a specific brightness corresponding to a color included in the color table.

A third control parameter of a third control unit serves e.g. for actuating the objective lens, the latter being used to set the focusing of the primary electron beam onto the object.

A fourth control parameter for actuating a fourth control unit serves to center the primary electron beam in the objective lens. By way of example, the fourth control unit serves to set electrostatic and/or magnetic units of the electron beam apparatus, by means of which the centering of the primary electron beam in the objective lens is set.

Moreover, the image quality of an image of the object and/or the quality of the representation of the detection signals based on the detected interaction radiation is/are influenced by a fifth control parameter of a fifth control unit for controlling and setting electrostatic and/or magnetic deflection units which are used in the electron beam apparatus for a so-called "beam shift". As a result of this, it is possible to set the position of the scanning region and optionally displace the scanning region to a desired position. This may occur without the use of a sample stage (also referred to as object holder below), on which the object is arranged. By way of example, if the scanning region migrates out of the actual region of the object observed by means of the electron beam apparatus on account of a change in the settings on the electron beam apparatus, the primary electron beam is displaced in such a way as a result of translational movements in the case of a "beam shift" that the scanning region once again lies in the desired observed region.

A stigmator used in an electron beam apparatus may also influence the image quality of the image of the object and/or the quality of the representation of the detection signals based on the detected interaction radiation. The stigmator—a magnetic and/or electrostatic multi-pole element—is used, in particular, for correcting an astigmatism. The stigmator may be set by a sixth control unit by means of a sixth control parameter.

The image quality of an image of the object and/or the quality of the representation of the detection signals based on the detected interaction radiation may however also be influenced by the position of a mechanically displaceable unit of the electron beam apparatus. By way of example, the image quality is influenced by the position of an aperture which is used to shape and delimit the primary electron beam in the electron beam apparatus.

The image quality of an image of the object and/or the quality of the representation of the detection signals based on the detected interaction radiation may further be influenced by the so-called scan rotation. This is a rotation of the scanning region in the plane of the scanning region about an optical axis of the electron beam apparatus.

Therefore, in order to obtain a desired image quality of an image of an object and/or a desired quality of the representation of the detection signals based on the detected interaction radiation, the user should take into account as many of the aforementioned control parameters as possible and/or further control parameters not specified here, with the physical effects obtained by the individual control parameters influencing one another in turn. The applicant is aware of the following procedures for ascertaining suitable values of the control parameters, by means of which a desired image quality and/or quality of the representation of the detection signals based on the detected interaction radiation may be obtained. By way of example, mathematical models may be used to ascertain suitable values of the individual control parameters in order to obtain a desired image quality and/or quality of the representation of the detection signals based on the detected interaction radiation. However, these calculated and theoretical values of the control parameters are often not suited to obtain a really good image quality and/or good representation of the detection signals based on the detected interaction radiation. This may be due to the fact that, for example, not all control parameters are taken into account in the mathematical models and/or the mathematical models are based on simplified assumptions which are more complicated in reality. In a further known method, provision is made for ascertaining the values of the various control parameters by experiment, with, for example, a reference sample being used for ascertainment by experiment. The ascertained values of the control parameters are used to set the control units of the electron beam apparatus. However, it is disadvantageous that an object to be examined and imaged does not always correspond to the reference sample, in particular in respect of the material composition and the topography. This may lead to optical aberrations and hence to a deterioration in the image quality which is actually obtained. A further known method lies in setting the image quality and/or the representation of the detection signals based on the detected interaction radiation by means of a manual search for the desired image quality for an object to be imaged and/or for the desired representation of the detection signals based on the detected interaction radiation. Here, the desired landing energy of the electrons, with which the electrons of the primary electron beam are incident on the object to be examined, is selected first. Subsequently, the brightness, the contrast, the focusing, the centering of the primary electron beam in the objective lens, the beam shift and/or the position of the adjustable unit are varied and matched to one another by trials in such a way until the desired image quality and/or the desired representation is/are obtained. Such a procedure is very complicated, as it has to be carried out for each setting of the landing energy.

It is therefore desirable to be able to provide a method and a particle beam apparatus for carrying out the method, by means of which values of control parameters for control units for actuating components of a particle beam apparatus are easy to ascertain, with the values of the control parameters ensuring a desired image quality of an image of an object and/or a desired representation of the detection signals based on the detected interaction radiation.

SUMMARY OF THE INVENTION

The system described herein serves to generate an image of an object and/or a representation of data about the object (for example a radiation spectrum, in particular an x-ray spectrum) using a particle beam apparatus. The particle beam apparatus comprises at least one beam generator for generating a particle beam comprising charged particles. By way of example, the charged particles are electrons or ions. Further, the particle beam apparatus comprises at least one guide unit for guiding the particle beam onto the object. A guide unit is understood to mean any unit for guiding the particle beam onto the object, but also units for shaping the particle beam which is then guided to the object. By way of example, the guide unit is embodied as an objective lens for focusing the particle beam onto the object, as an electrostatic and/or magnetic unit for beam shaping or for beam guidance, as a stigmator, as a condenser lens or as a mechanically adjustable aperture unit, by means of which the particle beam is delimited.

The charged particles have a landing energy when they are incident on the object. Expressed differently, the landing energy of the charged particles is the energy with which the object is examined and/or imaged. The landing energy of the charged particles may differ from the energy with which the charged particles are guided through a beam column of the particle beam apparatus. In particular, provision is made for initially accelerating the charged particles very strongly and only decelerating the latter to the landing energy just before incidence on the object. This was already explained further above. Complete reference is made thereto. By way of example, the landing energy of the charged particles lies in the range between 1 eV and 30 keV.

The particle beam apparatus also comprises at least one control unit for setting the guide unit by selecting at least one control parameter of the control unit. By way of example, the control parameter is a physical variable, in particular a control current or a control voltage, but also e.g. the ratio of physical variables, in particular an amplification of physical variables. The values of the physical variables are adjustable at the control unit or using the control unit and these control and/or feed the guide unit of the particle beam apparatus in such a way that desired physical effects, for example, the generation of specific magnetic fields and/or electrostatic fields, are brought about.

Moreover, the particle beam apparatus comprises at least one detector for detecting interaction particles and/or interaction radiation which emerges/emerge from an interaction between the particle beam and the object when the particle beam is incident on the object. By way of example, the interaction particles are secondary particles emitted by the object, e.g. secondary electrons, particles scattered back at the object, which are also referred to as backscattered particles, and/or scattered particles which e.g. are transmitted through the object in the beam direction. By way of example, the backscattered particles are backscattered electrons. By way of example, the interaction radiation is x-ray radiation or cathodoluminescence. By way of example, a radiation detector is used to detect the interaction radiation.

Further, the particle beam apparatus comprises at least one display unit for displaying an image of the object and/or a representation of data about the object, wherein the image and/or the representation is/are generated by means of detection signals which are generated by detecting the interaction particles and/or interaction radiation.

The method according to the system described herein comprises the step of setting the landing energy of the charged particles to a first value from a predeterminable range of the landing energy of the charged particles. By way of example, the predeterminable range lies between 1 eV and 30 keV, including the range boundaries. However, the predeterminable range of the landing energy of the charged particles is not restricted to these values. Rather, the predeterminable range may include any suitable value which is suitable for the invention.

Further, the method according to the system described herein comprises the step of setting a first control parameter value of the control parameter, at which a first image of the object with a desired image quality and/or a first desired representation of data about the object is/are obtained. Expressed differently, the first control parameter value of the control parameter is selected in such a way that e.g. an image of the object with a good image quality is created such that a user is able to analyze the object to be examined well on account of the image and the image information contained therein. Here, the image quality may be determined by means of e.g. objective criteria. By way of example, the image quality of an image becomes better with increasing resolution in the image. Alternatively, the image quality may be determined on the basis of subjective criteria. Here, a user determines individually as to whether or not an obtained image quality is sufficient. However, what may by all means occur in this case is that the image quality deemed sufficient by a first user is not considered sufficient by a second user. Alternative or additional options for determining the image quality are explained further above. These options are also explicitly referred to here. As explained, provision is additionally or alternatively made for the first control parameter value of the control parameter to be selected in such a way that a desired representation of data about the object (in particular a radiation spectrum) is obtained. The desired representation has a desired quality. By way of example, the quality of the representation is influenced by the count rate of the detected x-ray quanta on the one hand and, on the other hand, by the full width at half maximum of the measured peaks in an x-ray spectrum. The quality of the representation of the detection signals increases with higher count rate and smaller full width at half maximum. By way of example, if cathodoluminescence is detected by a radiation detector, the quality of the representation is then determined e.g. by a good detection signal of the radiation detector. By way of example, the quality of the representation is determined by the count rate of the detected photons of the cathodoluminescence. Here too, reference is made to the explanations made further above; these are explicitly referred to here. What was stated above may be summarized as follows: data with information about the object are captured in the case of a first control parameter set.

In the method according to the system described herein, the two aforementioned steps are repeated at least once, but with a different value of the landing energy. Expressed differently, the method according to the system described herein further comprises setting the landing energy of the charged particles to a second value from the predeterminable range of the landing energy. Further, the method according to the system described herein comprises setting a second control parameter value of the control parameter, at which a second image of the object with a desired image quality and/or a second desired representation of data about the object is/are obtained. What was stated above may be summarized as follows: data with information about the object are captured in the case of a second control parameter set.

By way of example, the control parameter of the control unit sets the contrast in the generated image or the brightness in the generated image. By way of example, the control parameter may also be used for actuating the objective lens, which is used to set the focusing of the particle beam onto the object. Further, the control parameter may also be used to set electrostatic and/or magnetic units of the particle beam apparatus, by means of which the centering of the primary electron beam in the objective lens is set. Moreover, the control parameter may also be used to control and set electrostatic and/or magnetic deflection units which are used in the particle beam apparatus for a "beam shift". A stigmator used in the particle beam apparatus may also be set by means of the control parameter. Further, the control parameter may also be used to set the position of a mechanically displaceable unit of the particle beam apparatus. Moreover, the control parameter may also be used to set a condenser lens arranged in the particle beam apparatus. A voltage at a collector grid of the detector may also be set by means of the control parameter. Further, by actuating a scanning device by way of the control parameter, it is also possible to set the scanning speed with which the particle beam may be scanned over the object.

Further, the method according to the system described herein now also comprises determining a functional relationship between the first control parameter value and the second control parameter value depending on the predeterminable range of the landing energy. Here, the functional relationship may be determined by different methods, which are explained in more detail below. The functional relationship may be a linear relationship or a nonlinear relationship. A step function may by all means also be comprised by the functional relationship or form the functional relationship. Accordingly, a functional relationship between the first control parameter value and the second control parameter value depending on the predeterminable range of the landing energy is now ascertained in accordance with the system described herein.

Once the aforementioned functional relationship has been determined, it is possible, by way of the determined functional relationship, to ascertain a corresponding value of the control parameter for each desired and settable value of the predeterminable range of the landing energy. In this respect, the method according to the system described herein comprises setting the landing energy to a desired value of the landing energy from the predeterminable range of the landing energy. Expressed differently, a user selects, from the predeterminable range of the landing energy of the charged particles, the landing energy of the charged particles with which he desires to examine and image the object. As a result of the determined functional relationship, it is possible to very quickly ascertain the value of the control parameter which corresponds to the desired value of the landing energy and which is used to actuate the guide unit. Subsequently, the object may be imaged and/or data about the object may be ascertained. The obtained image quality of the image and/or the obtained representation of data about the object is/are then sufficiently good, as desired by the user for the further analysis of the object.

In one exemplary embodiment, the functional relationship may also be determined on the basis of more than two control parameter values. In particular, provision is made for ascertaining a multiplicity of control parameter values, at which a good image quality and/or a good representation of data about the object is/are obtained. By way of example, the multiplicity is more than three control parameter values, more than eight control parameter values or more than ten control parameter values.

The further method according to the system described herein comprises the step of setting a distance between the guide unit and a surface region of the object, with the particle beam being incident on the surface region. By way of example, if the guide unit is embodied as an objective lens which focuses the particle beam onto the object, then the distance described above is the distance between the objective lens and the surface region of the object onto which the particle beam is focused. Said distance is also referred to as working distance. By way of example, the predeterminable range lies in the range from 0.3 mm to 20 mm or in the range from 0.5 mm to 12 mm. The range limits are included in the predeterminable range. Reference is explicitly made to the fact that the aforementioned distance values should only be understood to be exemplary and not restrictive. Instead, other values for the distance may also be selected. By way of example, the distance is set by means of an object holder designed in a movable fashion, on which the object is arranged. By way of example, the object holder is embodied to be movable in three directions which are arranged perpendicular to one another. Further, the object holder may e.g. be rotated about a first axis of rotation and/or about a second axis of rotation. By way of example, the first axis of rotation and the second axis of rotation are arranged perpendicular to one another.

Further, the further method according to the system described herein comprises the step of setting a first control parameter value of the control parameter, at which a first image of the object with a desired image quality and/or a first desired representation of data about the object is/are obtained. Expressed differently, the first control parameter value of the control parameter is selected in such a way that e.g. an image of the object with a good image quality is created such that a user is able to analyze the object to be examined well on account of the image and the image information contained therein. Additionally or alternatively, provision is made for the first control parameter value of the control parameter to be selected in such a way that a desired representation of data about the object (in particular a radiation spectrum) is obtained. Reference is made to the remarks further above in respect of the possibility of determining the image quality and/or the quality of the representation. This is referred to in full here.

In the further method according to the system described herein, the two aforementioned steps are repeated at least once, but with a different value of the distance. Expressed differently, the further method according to the system described herein further comprises setting the distance to a second value from the predeterminable range of the distance. Further, the further method according to the system described herein comprises setting a second control parameter value of the control parameter, at which a second image of the object with a desired image quality and/or a second desired representation of data about the object is/are obtained.

By way of example, the control parameter of the control unit also sets the contrast in the generated image or the brightness in the generated image in this case. By way of example, the control parameter may also be used for actuating the objective lens, which is used to set the focusing of the particle beam onto the object. Further, the control parameter may also be used to set electrostatic and/or magnetic units of the particle beam apparatus, by means of which the centering of the primary electron beam in the objective lens is set. Moreover, the control parameter may be used to control and set electrostatic and/or magnetic deflection units which are used in the particle beam apparatus for a "beam shift". A stigmator used in the particle beam apparatus may also be set by means of the control parameter. Further, the control parameter may also be used to set the position of a mechanically displaceable unit of the particle beam apparatus. Moreover, the control parameter may also be used to set a condenser lens arranged in the particle beam apparatus. A voltage at a collector grid of the detector may also be set by means of the control parameter. Further, by actuating a scanning device by way of the control parameter, it is also possible to set the scanning speed with which the particle beam may be scanned over the object.

Further, the further method according to the system described herein now also comprises determining a functional relationship between the first control parameter value and the second control parameter value depending on the predeterminable range of the distance. Here, the functional relationship may be determined by different methods, which are explained in more detail below. The functional relationship may be a linear relationship or a nonlinear relationship. A step function may by all means also be comprised by the functional relationship or form the functional relationship. Accordingly, a functional relationship between the first control parameter value and the second control parameter value depending on the predeterminable range of the distance is now ascertained in accordance with the system described herein.

Once the aforementioned functional relationship has been determined, it is possible, by way of the determined functional relationship, to ascertain a corresponding value of the control parameter for each desired and settable value of the predeterminable range of the distance. In this respect, the method according to the system described herein comprises setting the distance to a desired value of the distance from the predeterminable range of the distance. Expressed differently, a user selects, from the predeterminable range of the distance, the distance with which he desires to examine and image the object. As a result of the determined functional relationship, it is possible to very quickly ascertain the value of the control parameter which corresponds to the desired value of the distance and which is used to actuate the guide unit. Subsequently, the object may be imaged and/or examined. The obtained image quality of the image and/or the obtained representation of data about the object is/are then sufficiently good, as desired by the user for the further analysis of the object.

Here too, the functional relationship may also be determined, once again, on the basis of more than two control parameter values in one exemplary embodiment. In particular, provision is made for ascertaining a multiplicity of control parameter values, at which a good image quality and/or a desired representation of data about the object is/are obtained. By way of example, the multiplicity is more than three control parameter values, more than eight control parameter values or more than ten control parameter values.

The system described herein is based on the surprising discovery that it is possible to determine a functional relationship between the control parameter values and the landing energy or the distance by recording a few images or representations, which each have a sufficient desired quality, and by determining the values of the control parameter and of the landing energy or of the distance leading to these images or representations. As a result of this functional relationship, it is then possible to calculate the associated control parameter value for each desired value of the landing energy or for each desired value of the distance in order to obtain a desired image quality in the image and/or a desired representation of data about the object. Using the method according to the system described herein, it is possible to obtain a desired image quality of the image and/or a desired representation of data about the object much more quickly than with the methods known from the prior art. Also, in particular, it is possible, in an automated fashion, to record numerous images or representations at different values of the landing energy or of the distance with the corresponding control parameter values such that a sufficiently good image quality of all recorded images and/or a sufficient quality of all representations of data about the object is/are obtained at all times.

By way of example, the functional relationship may be determined by an interpolation. Any suitable interpolation method, for example a linear interpolation, a nonlinear interpolation, a trigonometric interpolation, a logarithmic interpolation and/or a spline interpolation, may be used in the interpolation. In addition and/or as an alternative thereto, provision is made for determining the functional relationship by extrapolation. Any suitable extrapolation method, for example a linear extrapolation, a nonlinear extrapolation, a trigonometric extrapolation and/or a logarithmic extrapolation, may be used in the extrapolation. As an alternative or in addition thereto, the functional relationship may be determined by forming an average, ascertaining random values and/or determining the smallest value or the largest value from the set of the first value and second value.

In an embodiment of the method according to the system described herein, the particle beam apparatus comprises at least one memory unit. Further, the method according to the system described herein additionally or alternatively comprises the following steps: the first control parameter value and the first value of the landing energy are stored in the memory unit. Further, the second control parameter value and the second value of the landing energy are stored in the memory unit. Moreover, the first control parameter value, the first value of the landing energy, the second control parameter value and the second value of the landing energy are read from the memory unit before determining the functional relationship. In the further method according to the system described herein, provision is additionally or alternatively made for the first control parameter value and the first value of the distance to be stored in the memory unit. Further, the second control parameter value and the second value of the distance are stored in the memory unit. Moreover, the first control parameter value, the first value of the distance, the second control parameter value and the second value of the distance are read from the memory unit before determining the functional relationship. These embodiments are based on the discovery that settings for images with a good image quality and/or for good representations of data about the object, i.e. the values of the control parameters and the associated landing energy values or distances, are initially stored before the functional relationship is determined between the control parameter values and the landing energy or the distance.

In a further embodiment of the method according to the system described herein, provision is additionally or alternatively made for the functional relationship to be stored in the memory unit.

In an in turn further exemplary embodiment of the method according to the system described herein, the corresponding value of the control parameter is additionally or alternatively calculated for each value of the predeterminable range of the landing energy of the charged particles by means of the determined functional relationship. Each value of the predeterminable range of the landing energy and the value of the control parameter which corresponds to this value and has now been calculated are stored in the memory unit. Such an exemplary embodiment is also provided in the further method according to the system described herein. Thus, in the further method according to the system described herein, the corresponding value of the control parameter is additionally or alternatively calculated for each value of the predeterminable range of the distance by means of the determined functional relationship. Each value of the predeterminable range of the distance and the value of the control parameter which corresponds to this value and has now been calculated are stored in the memory unit. In principle, storing is carried out at least as a number tuple, for example as a 2-tuple. If the user now wishes to generate an image and/or a representation of data about the object with a specific landing energy of the charged particles or with a specific distance, the corresponding value of the control parameter is read from the memory unit and fed to the control unit such that the guide unit is operated with the corresponding value of the control parameter.

In an even further exemplary embodiment of the two methods according to the system described herein, provision is additionally or alternatively made for the first control parameter value and/or the second control parameter value to be used for controlling at least one of the following units:
    an amplifier of the detector for amplifying the detection signal in order to set the contrast and/or the brightness,
    the already aforementioned objective lens for focusing the particle beam,
    the already aforementioned at least one electrostatic and/or magnetic unit, with the latter e.g. being used for centering the primary electron beam in the objective lens, for setting the scanning speed of the particle beam when scanning the particle beam over the object or for setting a "beam shift", the already aforementioned stigmator, the already aforementioned mechanically adjustable aperture unit, the already aforementioned condenser lens, and the already aforementioned collector grid of the detector.

As already explained above, the functional relationship may also be determined by means of more than two set control parameter values. Thus, provision is additionally made in a further exemplary embodiment of the method according to the system described herein for the landing energy of the charged particles to be set to a third value from the predeterminable range of the landing energy. Further, a third control parameter value of the control parameter is set, at which a third image of the object with the desired image quality and/or a third desired representation of data about the object is/are obtained. The functional relationship is also determined additionally taking into account the third control parameter value and the associated third value of the landing energy. Such an exemplary embodiment is also provided in the further method according to the system described herein. Thus, provision is additionally made for the distance to be set to a third value from the predeterminable range of the distance. Further, a third control parameter value of the control parameter is set, at which a third image of the object with the desired image quality and/or a third desired representation of data about the object is/are obtained. Now, the functional relationship is also determined additionally taking into account the third control parameter value and the associated third value of the distance.

Accordingly, it is also possible to use more control parameter values, for example 5, 7 or 11 control parameter values, for determining the functional relationship. Should the image quality/data quality at a calculated control parameter value not be sufficient against expectations, provision is made for setting the image quality/data quality manually in an exemplary embodiment. This set control parameter value is additionally used for all subsequent calculations of the control parameter values such that the image quality/data quality in the surroundings of this control parameter value has an increased quality.

In a further embodiment of the system described herein, provision is made for use to be made of not only one control parameter but of at least two control parameters when generating the image. By way of example, this occurs simultaneously. By way of example, up to four or up to eight control parameters are used. Accordingly, provision is made in this exemplary embodiment for use to be made of at least two control parameters which actuate at least two of the following units or set at least two of the following variables: the contrast in the generated image, the brightness in the generated image, the objective lens, at least one of the electrostatic and/or magnetic units of the particle beam apparatus for centering the primary electron beam in the objective lens, at least one of the electrostatic and/or magnetic deflection units of the particle beam apparatus for setting the "beam shift", the stigmator, at least one mechanically displaceable unit of the particle beam apparatus, the condenser lens, the collector grid of the detector and the scanning speed with which the particle beam is scanned over the object. Expressed more generally, provision is additionally or alternatively made in this embodiment of the method according to the system described herein for the guide unit of the particle beam apparatus to be a first guide unit, the control parameter to be a first control parameter and the control unit to be a first control unit for setting the first guide unit. Further, the particle beam apparatus comprises at least one second guide unit for guiding the particle beam onto the object. Moreover, the particle beam apparatus comprises at least one second control unit for setting the second guide unit by selecting a value of a second control parameter of the second control unit. In the exemplary embodiment of the method according to the system described herein, a first control parameter value of the second control parameter is set after setting the landing energy to the first value from the predeterminable range of the landing energy, the first image of the object with a desired image quality and/or the first desired representation of data about the object being obtained at said first control parameter value. Moreover, a second control parameter value of the second control parameter is set after setting the landing energy to the second value from the predeterminable range of the landing energy, the second image of the object with a desired image quality and/or the second desired representation of data about the object being obtained at said second control parameter value. Further, a further functional relationship is determined between the first control parameter value of the second control parameter and the second control parameter value of the second control parameter depending on the predeterminable range of the landing energy. The value of the second control parameter corresponding to the desired value of the landing energy is selected on the basis of the determined further functional relationship after setting the landing energy to a desired value of the landing energy from the predeterminable range of the landing energy. Further, the second guide unit is controlled with the value of the second control parameter corresponding to the desired value of the landing energy.

Analog statements apply to the exemplary embodiment of the further method according to the system described herein. Thus, a first control parameter value of the second control parameter is set after setting the distance to the first value from the predeterminable range of the distance, the first image of the object with a desired image quality and/or the first desired representation of data about the object being obtained at said first control parameter value. Moreover, a second control parameter value of the second control parameter is set after setting the distance to the second value from the predeterminable range of the distance, the second image of the object with a desired image quality and/or the second desired representation of data about the object being obtained at said second control parameter value. Further, a further functional relationship is determined between the first control parameter value of the second control parameter and the second control parameter value of the second control parameter depending on the predeterminable range of the distance. The value of the second control parameter corresponding to the desired value of the distance is selected on the basis of the determined further functional relationship after setting the distance to a desired value of the distance from the predeterminable range of the distance. Further, the second guide unit is controlled with the value of the second control parameter corresponding to the desired value of the distance.

The system described herein also relates to a computer program product comprising program code, which can be loaded or is loaded into a processor of a particle beam apparatus, wherein the program code, when executed in the processor, controls the particle beam apparatus in such a way that a method having at least one of the aforementioned or following features or having a combination of at least two of the aforementioned or following features is carried out.

The system described herein further relates to a particle beam apparatus for generating an image of an object and/or a representation of data about the object, wherein the particle beam apparatus is already explained above and will be specified in more detail below. This will be briefly summarized below. The particle beam apparatus according to the system described herein comprises at least one beam generator for generating a particle beam comprising charged particles. The charged particles are electrons or ions, for example. The particle beam apparatus also comprises an object holder designed in a movable fashion, at which the object may be arranged. Further, the particle beam apparatus comprises at least one guide unit for guiding the particle beam onto the object. Upon incidence on the object, the charged particles have a landing energy, as already explained further above. Moreover, the particle beam apparatus according to the system described herein comprises at least one control unit for setting the guide unit by selecting a value of a control parameter of the control unit. Further, the particle beam apparatus comprises at least one detector for detecting interaction particles and/or interaction radiation which emerges/emerge from an interaction between the particle beam and the object when the particle beam is incident on the object. Further, the particle beam apparatus according to the system described herein is provided with at least one display unit for displaying an image of the object and/or a representation of data about the object, wherein the image and/or the representation is/are generated on the basis of detection signals which are generated by the detected interaction particles and/or interaction radiation. Moreover, the particle beam apparatus comprises a processor, in which a computer program product with the features already mentioned further above is loaded.

In a further embodiment of the particle beam apparatus according to the system described herein, the guide unit comprises at least one of the following features:
- the already aforementioned objective lens for focusing the particle beam,
- the already aforementioned at least one electrostatic and/or magnetic unit, with the latter e.g. being used for centering the primary electron beam in the objective lens, for setting the scanning speed of the particle beam when scanning the particle beam over the object or for setting a "beam shift",
- the already aforementioned stigmator,
- the already aforementioned mechanically adjustable aperture unit, and
- the already aforementioned condenser lens.

In a further exemplary embodiment of the particle beam apparatus according to the system described herein, the beam generator is embodied as a first beam generator and the particle beam is embodied as a first particle beam comprising first charged particles. The guide unit is embodied as a first guide unit for guiding the first particle beam onto the object. Further, the particle beam apparatus according to the system described herein comprises at least one second beam generator for generating a second particle beam comprising second charged particles. Moreover, the particle beam apparatus according to the system described herein comprises at least one second guide unit for guiding the second particle beam onto the object.

In particular, provision is made for the particle beam apparatus to be embodied as an electron beam apparatus and/or as an ion beam apparatus.

BRIEF DESCRIPTION OF DRAWINGS

Further embodiments and advantages of the system described herein are described below in conjunction with the drawings. In the figures.

DETAILED DESCRIPTION OF VARIOUS EMBODIMENTS

The system described herein is now explained in more detail by means of particle beam apparatuses in the form of an SEM and in the form of a combination apparatus, which has an electron beam column and an ion beam column. Reference is explicitly made to the fact that the system described herein may be used in any particle beam apparatus, in particular in any electron beam apparatus and/or in any ion beam apparatus.

Figure 1:
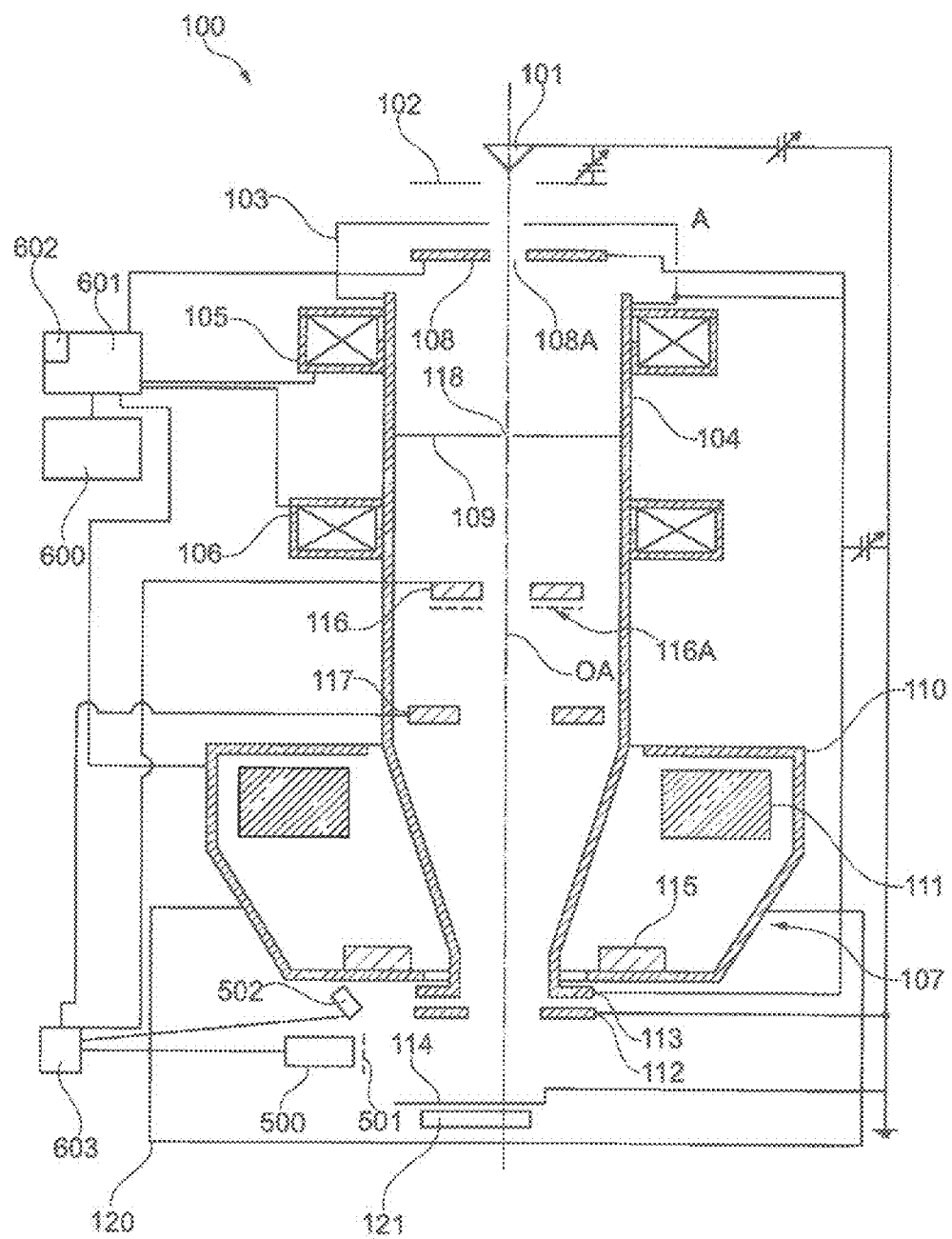
FIG. 1 shows a first embodiment of a particle beam apparatus according to the system described herein.

FIG. 1 shows a schematic illustration of an SEM 100. The SEM 100 comprises a first beam generator in the form of an electron source 101, which is embodied as a cathode. Further, the SEM 100 is provided with an extraction electrode 102 and with an anode 103, which is placed onto one end of a beam guiding tube 104 of the SEM 100. By way of example, the electron source 101 is embodied as thermal field emitter. However, the invention is not restricted to such an electron source 101. Rather, any electron source is utilizable.

Electrons emerging from the electron source 101 form a primary electron beam. The electrons are accelerated to the anode potential due to a potential difference between the electron source 101 and the anode 103. By way of example, in the exemplary embodiment depicted here, the anode potential is 1 kV to 20 kV, e.g. 5 kV to 15 kV, in particular 8 kV, in relation to a ground potential of a housing of a sample chamber 120. However, alternatively it can be at ground potential.

A condenser lens 105 is arranged at the beam guiding tube 104. Further, provision is made of a stigmator 106. Here, proceeding from the electron source 101 as viewed in the direction of a first objective lens 107, the condenser lens 105 is arranged first, followed by the stigmator 106. Reference is explicitly made to the fact that further embodiments of the SEM 100 may also have more than one condenser lens. A first aperture unit 108, which may also be embodied as a pressure stage aperture in some embodiments, is arranged between the anode 103 and the condenser lens 105. Together with the anode 103 and the beam guiding tube 104, the first aperture unit 108 is at a high voltage potential, namely the potential of the anode 103, or it is connected to ground. The first aperture unit 108 has numerous first apertures 108A, of which one is depicted in FIG. 1. Two first apertures 108A are present, for example. Each one of the numerous first apertures 108A has a different aperture diameter. By means of an adjustment mechanism (not depicted here), it is possible to set a desired first aperture 108A on an optical axis OA of the SEM 100 and center the latter, i.e. obtain an alignment in respect of the optical axis OA that is as central as possible. Reference is explicitly made to the fact that, in further embodiments, the first aperture unit 108 may be provided with only a single aperture 108A. An adjustment mechanism for centering the first aperture unit 108 is likewise provided in this embodiment.

A stationary second aperture unit 109 is arranged between the condenser lens 105 and the stigmator 106. The second aperture unit 109 may be designed in a movable fashion as an alternative thereto.

The first objective lens 107 comprises pole pieces 110, in which a centrally arranged bore is embodied along the optical axis OA. The beam guiding tube 104 is guided through this bore. Further, coils 111 are arranged in the pole pieces 110.

An electrostatic retardation device is arranged in a lower region of the beam guiding tube 104. It has a single electrode 112 and a tube electrode 113. The tube electrode 113 is arranged at one end of the beam guiding tube 104, which faces an object 114. Together with the beam guiding tube 104, the tube electrode 113 is at the potential of the anode 103, while the single electrode 112 and the object 114 are at a lower potential in relation to the potential of the anode 103. In the present case, this is the ground potential of the housing of the sample chamber 120. In this manner, the electrons of the primary electron beam may be decelerated to a desired energy which is required for examining the object 114. The desired energy is the examination energy. It is also referred to as landing energy.

The SEM 100 further comprises a scanning device 115, by means of which the primary electron beam may be deflected and scanned over the object 114. Here, the electrons of the primary electron beam interact with the object 114. As a consequence of the interaction, interaction particles and/or interaction radiation emerge/emerges, which is/are detected. In particular, electrons are emitted from the surface of the object 114—the so-called secondary electrons—or electrons of the primary electron beam are scattered back—the so-called backscattered electrons—as interaction particles.

The object 114 and the individual electrode 112 may also be at different potentials and potentials different than ground. It is thereby possible to set the location of the retardation of the primary electron beam in relation to the object 114. By way of example, if the retardation is carried out very near to the object 114, optical aberrations become smaller.

A detector arrangement comprising a first detector 116 and a second detector 117 is arranged in the beam guiding tube 104 for detecting the secondary electrons and/or the backscattered electrons. Here, the first detector 116 is arranged on the source-side along the optical axis OA, while the second detector 117 is arranged on the object-side along the optical axis OA in the beam guiding tube 104. The first detector 116 and the second detector 117 are arranged offset from one another in the direction of the optical axis OA of the SEM 100. Both the first detector 116 and the second detector 117 each have a passage opening, through which the primary electron beam may pass. The first detector 116 and the second detector 117 are approximately at the potential of the anode 103 and of the beam guiding tube 104. The optical axis OA of the SEM 100 extends through the respective passage openings.

The second detector 117 serves principally for detecting secondary electrons. Upon emerging from the object 114, the secondary electrons initially have a low kinetic energy and arbitrary directions of motion. By means of the strong extraction field emanating from the tube electrode 113, the secondary electrons are accelerated in the direction of the first objective lens 107. The secondary electrons enter the first objective lens 107 approximately parallel. The beam diameter of the beam of secondary electrons remains small in the first objective lens 107 as well. The first objective lens 107 then has a strong effect on the secondary electrons and generates a comparatively short focus of the secondary electrons with sufficiently steep angles with respect to the optical axis OA, such that the secondary electrons diverge far apart from one another downstream of the focus and impinge on the second detector 117 on the active area thereof. By contrast, only a small proportion of electrons that are backscattered at the object 114—that is to say backscattered electrons—which have a relatively high kinetic energy in comparison with the secondary electrons upon emerging from the object 114, are detected by the second detector 117. The high kinetic energy and the angles of the backscattered electrons with respect to the optical axis OA upon emerging from the object 114 have the effect that a beam waist, that is to say a beam region having a minimum diameter, of the backscattered electrons lies in the vicinity of the second detector 117. A large portion of the backscattered electrons passes through the passage opening of the second detector 117. Therefore, the first detector 116 substantially serves to detect the backscattered electrons.

In a further embodiment of the SEM 100, the first detector 116 may additionally be embodied with a retarding field grid 116A. The retarding field grid 116A is arranged at the side of the first detector 116 directed toward the object 114. With respect to the potential of the beam guiding tube 104, the retarding field grid 116A has such a negative potential that only backscattered electrons with a high energy pass through the retarding field grid 116A to the first detector 116. Additionally or alternatively, the second detector 117 has a further retarding field grid, which has an analogous embodiment to the aforementioned retarding field grid 116A of the first detector 116 and which has an analogous function.

The detection signals generated by the first detector 116 and the second detector 117 are used to generate an image or images of the surface of the object 114. These are displayed on a display unit 603 connected to the first detector 116 and the second detector 117.

Reference is explicitly made to the fact that the apertures of the first aperture unit 108 and of the second aperture unit 109, as well as the passage openings of the first detector 116 and of the second detector 117 are depicted in exaggerated fashion. The passage opening of the first detector 116 and of the second detector 117 have an extent perpendicular to the optical axis OA in the range of 0.5 mm to 5 mm. By way of example, they are of circular design and have a diameter in the range of 1 mm to 3 mm perpendicular to the optical axis OA.

The second aperture unit 109 is configured as a pinhole aperture in the exemplary embodiment depicted here and it is provided with a second aperture 118 for the passage of the primary electron beam, which has an extent in the range from 5 µm to 500 µm, e.g. 35 µm. As an alternative thereto, provision is made in a further embodiment for the second aperture unit 109 to be provided with a plurality of apertures, which can be displaced mechanically with respect to the primary electron beam or which can be reached by the primary electron beam by the use of electrical and/or magnetic deflection elements. The second aperture unit 109 is embodied as a pressure stage aperture. It separates a first region, in which the electron source 101 is arranged and in which an ultra-high vacuum ($10^{-6}$ Pa to $10^{-10}$ Pa) prevails, from a second region, which has a high vacuum ($10^{-1}$ Pa to $10^{-5}$ Pa). The second region is the intermediate pressure region of the beam guiding tube 104, which leads to the sample chamber 120.

A further detector in the form of an analysis device 500, which is likewise connected to the display unit 603, is arranged in the sample chamber 120. The analysis device comprises a collector grid 501 for guiding the interaction particles onto the analysis device 500. A potential is applied to the collector grid 501 in such a way that interaction particles reach the analysis device 500.

The SEM 100 further comprises a fourth detector 121, which is arranged in the sample chamber 120. More precisely, the fourth detector 121 is arranged behind the object 114, as seen from the electron source 101 along the optical axis OA. The primary electron beam passes through the object 114 to be examined. When the primary electron beam passes through the object 114 to be examined, the electrons of the primary electron beam interact with the material of the object 114 to be examined. The electrons passing through the object 114 to be examined or—in the case of a sufficiently thin object 114—the electrons emitted in the direction of the fourth detector 121 by the object 114 are detected by the fourth detector 121.

The SEM 100 comprises a processor 600, loaded onto which there is a computer program product with program code which controls the SEM 100. This is discussed in more detail further below. The processor 600 is connected to a control unit 601, said control unit comprising a memory unit 602. The control unit 601 serves to actuate at least one guide unit, for example, the first aperture unit 108, the condenser lens 105, the stigmator 106 and/or the first objective lens 107. This is discussed in more detail further below.

A radiation detector 502 with which interaction radiation arising on account of an interaction between the primary electron beam and the object 114 is detected is also arranged in the sample chamber 120. By way of example, the interaction radiation is x-ray radiation or cathodoluminescence. The radiation detector 502 is likewise connected to the display unit 603.

Figure 1A:
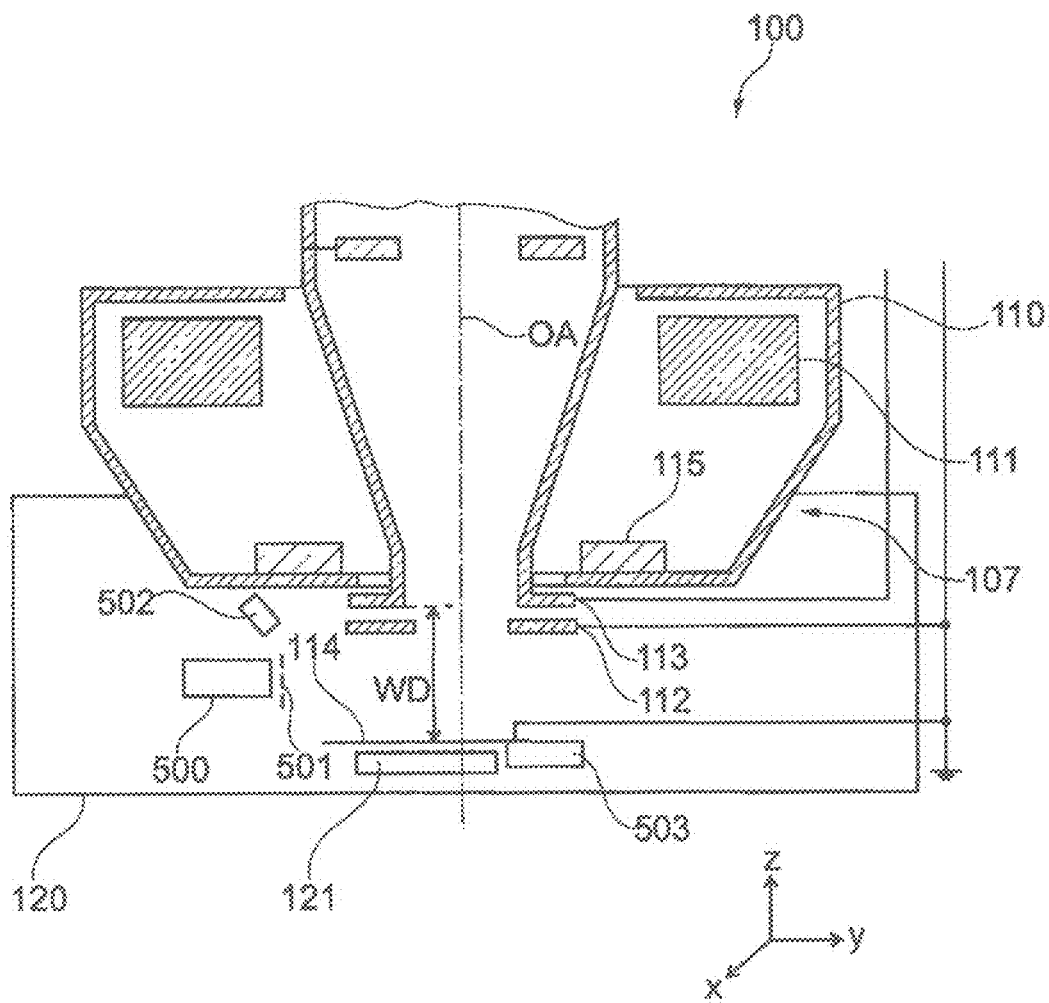
FIG. 1A shows a magnified illustration of a region of the particle beam apparatus in accordance with FIG. 1.

FIG. 1A shows a magnified illustration of the region of the sample chamber 120 of the SEM 100. FIG. 1A is based on FIG. 1. The same reference signs refer to the same components. In contrast to FIG. 1, FIG. 1A shows a sample carrier 503 (i.e. an object holder) designed in a movable fashion, the object 114 to be examined being arranged thereon. The sample carrier 503 is designed to be movable in three directions arranged perpendicular to one another, namely in an x-direction, in a y-direction and in a z-direction. Additionally, the sample carrier 503 may be rotated about a first axis of rotation and about a second axis of rotation arranged perpendicular to the first axis of rotation. It is possible to set the distance WD of the surface of the object 114 from the tube electrode 113 of the beam guiding tube 104 by means of a movement of the sample carrier in the z-direction, which extends parallel to the optical axis OA or corresponds to the latter. The tube electrode 113 forms the end of the beam guiding tube 104. The distance WD is also referred to as working distance. By way of example, it lies in the range from 0.3 mm to 20 mm or in the range from 0.5 mm to 12 mm. The range limits are included in the predeterminable range. Reference is explicitly made to the fact that the aforementioned distance values should only be understood to be exemplary and not restrictive. Instead, other values for the distance may also be selected.

Figure 2:
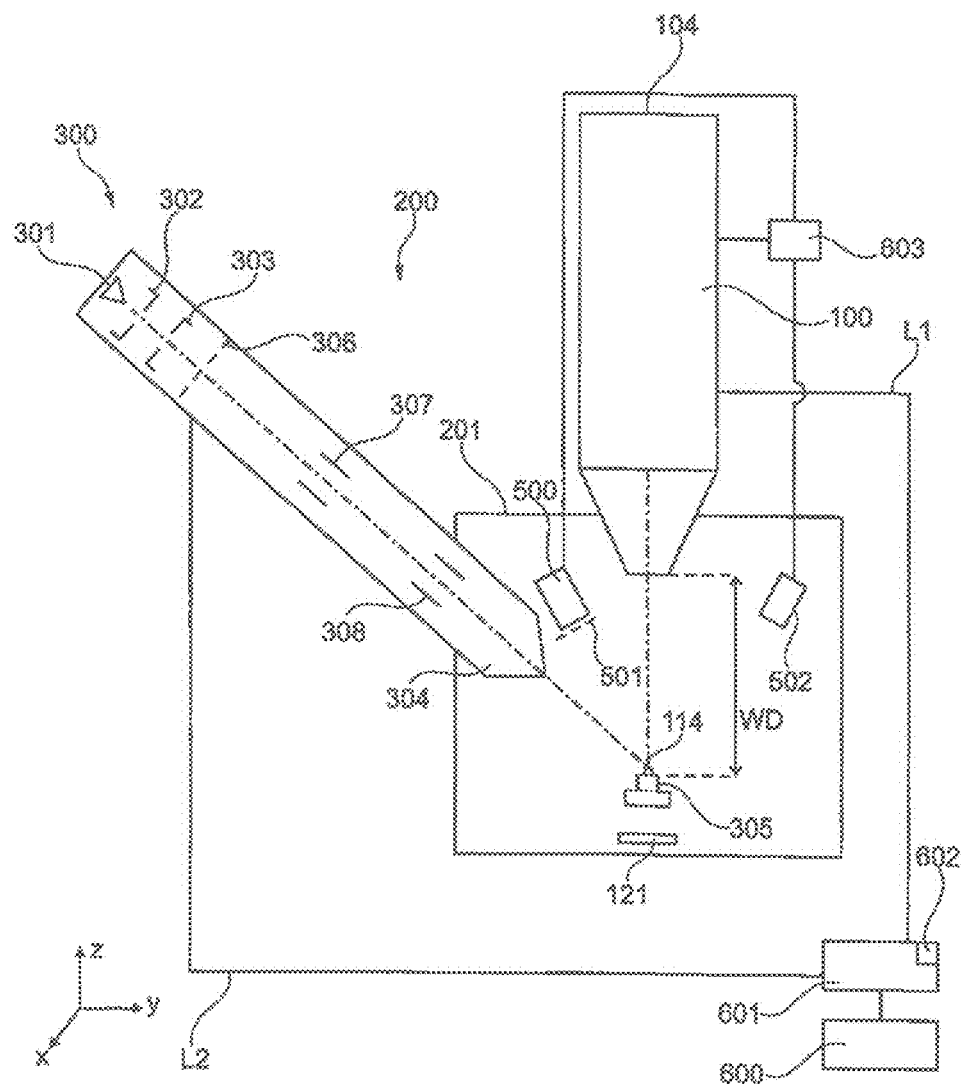
FIG. 2 shows a second embodiment of a particle beam apparatus according to the system described herein.

FIG. 2 shows a particle beam apparatus in the form of a combination apparatus 200. The combination apparatus 200 has two particle beam columns. On the one hand, the combination apparatus 200 is provided with the SEM 100, as already depicted in FIG. 1, but without the sample chamber 120. Rather, the SEM 100 is arranged at a sample chamber 201. The SEM 100 serves to generate a first particle beam, namely the primary electron beam already described further above. On the other hand, the combination apparatus 200 is provided with an ion beam apparatus 300, which is likewise arranged at the sample chamber 201.

The SEM 100 is arranged vertically in relation to the sample chamber 201. By contrast, the ion beam apparatus 300 is arranged inclined by an angle of approximately 54° in relation to the SEM 100. It has a second beam generator in the form of an ion beam generator 301. Ions, which form a second particle beam in the form of an ion beam, are generated by the ion beam generator 301. The ions are accelerated by means of an extraction electrode 302, which is at a predeterminable potential. The second particle beam then reaches through ion optics of the ion beam apparatus 300, wherein the ion optics comprise an ion condenser lens 303 and a second objective lens 304. The second objective lens 304 ultimately generates an ion beam, which is focused on the object 114 arranged on a sample holder 305.

An adjustable aperture 306, a first electrode arrangement 307 and a second electrode arrangement 308 are arranged above the objective lens 304 (i.e. in the direction of the ion beam generator 301), wherein the first electrode arrangement 307 and the second electrode arrangement 308 are embodied as scanning electrodes. The second particle beam is scanned over the surface of the object 114 by means of the first electrode arrangement 307 and the second electrode arrangement 308, with the first electrode arrangement 307 acting in a first direction and the second electrode arrangement 308 acting in a second direction, which is counter to the first direction. Using this, scanning is carried out in e.g. an x-direction. The scanning in a y-direction perpendicular thereto is brought about by further electrodes (not depicted here), which are rotated by 90°, at the first electrode arrangement 307 and at the second electrode arrangement 308.

The distances depicted in FIG. 2 between the individual units of the combination apparatus 200 are depicted in exaggerated fashion in order to better depict the individual units of the combination apparatus 200.

An analysis device 500 comprising a collector grid 501 is arranged in the sample chamber 201 and said analysis device detects interaction particles which arise on account of an interaction of the primary electron beam with the object 114 or on account of an interaction of the ion beam with the object 114. By way of example, the interaction particles are secondary electrons, backscattered electrons and/or secondary ions. The analysis device 500 is also connected to the display unit 603 in this exemplary embodiment, said display unit likewise being connected to the first detector 116 and the second detector 117 of the SEM 100.

The combination apparatus 200 likewise comprises a processor 600, loaded onto which there is a computer program product with program code which controls the SEM 100 and/or the ion beam apparatus 300. This is discussed in more detail further below. The processor 600 is also connected to the control unit 601 in this exemplary embodiment, said control unit comprising the memory unit 602. The control unit 601 serves to actuate at least one guide unit of the combination apparatus 200, for example one of the guide units, already mentioned above, of the SEM 100 or, for example, the condenser lens 303, the second objective lens 304 and/or the adjustable aperture 306 of the ion beam apparatus 300. The control unit 601 is connected to at least one of the guide units. This is depicted schematically by a first line L1 and a second line L2.

A radiation detector 502 with which interaction radiation arising on account of an interaction between the primary electron beam and the object 114 is detected is also arranged in the sample chamber 201. By way of example, the interaction radiation is, once again, x-ray radiation or cathodoluminescence. The radiation detector 502 is likewise connected to the display unit 603.

The sample carrier 305 is designed to be movable in three directions arranged perpendicular to one another, namely in an x-direction, in a y-direction and in a z-direction. Additionally, the sample carrier 305 may be rotated about a first axis of rotation and about a second axis of rotation arranged perpendicular to the first axis of rotation. It is possible to set the distance WD of the surface of the object 114 from the beam guiding tube 104 of the SEM 100 by means of a movement of the sample carrier 305 in the z-direction, which extends parallel to the optical axis OA of the SEM 100 or corresponds to the latter. This is the working distance. By way of example, it lies in the range from 0.3 mm to 20 mm or in the range from 0.5 mm to 12 mm in this case too. The range limits are included in the predeterminable range. Reference is explicitly made to the fact that the aforementioned distance values should only be understood to be exemplary and not restrictive. Instead, other values for the distance may also be selected.

Figure 3:
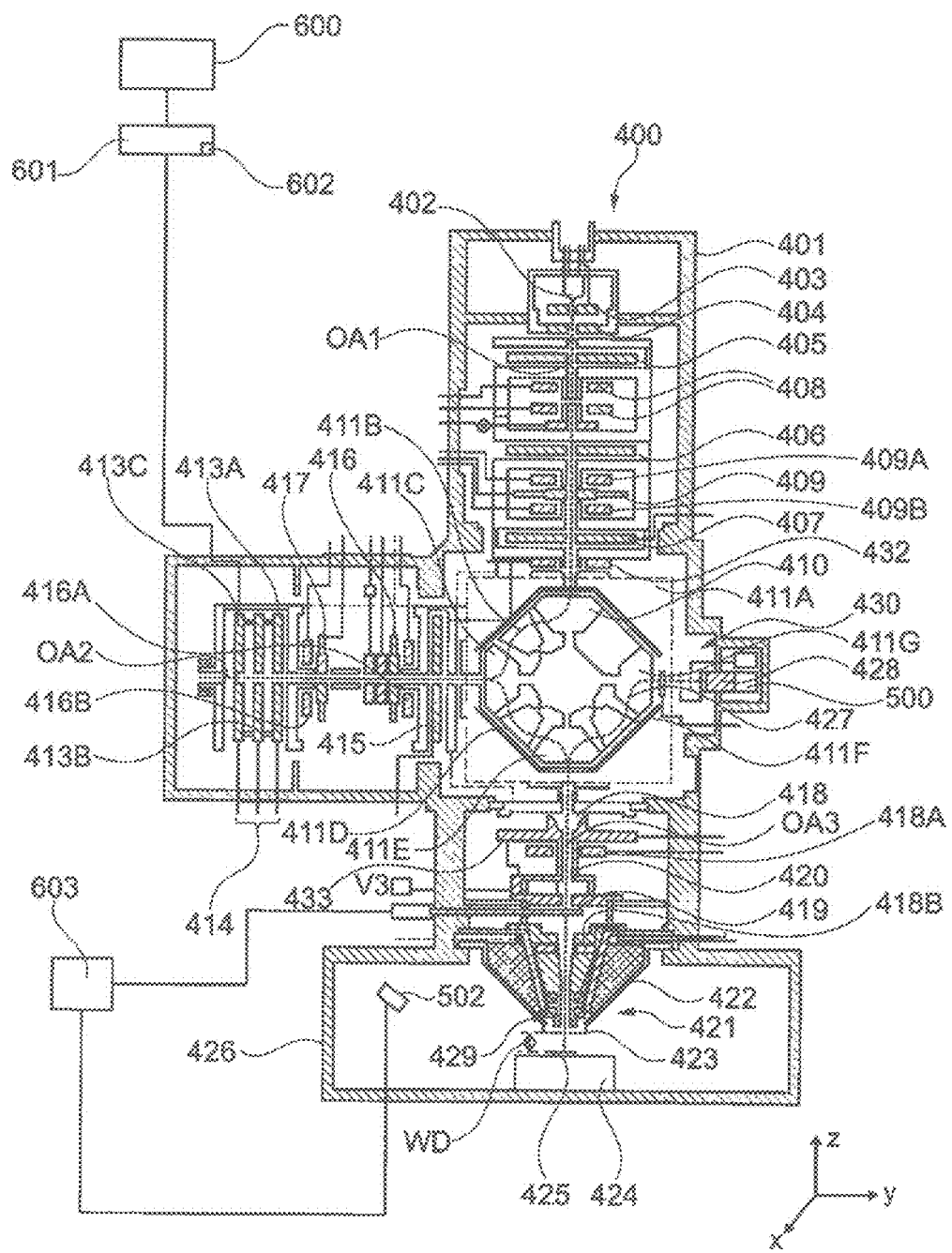
FIG. 3 shows a third embodiment of a particle beam apparatus according to the system described herein.

FIG. 3 is a schematic illustration of a further exemplary embodiment of a particle beam apparatus according to the system described herein. This exemplary embodiment of the particle beam apparatus is provided with the reference sign 400 and comprises a mirror corrector for correcting e.g. chromatic and/or spherical aberrations. The particle beam apparatus 400 comprises a particle beam column 401, which is embodied as an electron beam column and substantially corresponds to an electron beam column of a corrected SEM. However, the particle beam apparatus 400 is not restricted to an SEM with a mirror corrector. Rather, the particle beam apparatus may comprise any type of correction units.

The particle beam column 401 comprises a particle beam generator in the form of an electron source 402 (cathode), an extraction electrode 403, and an anode 404. By way of example, the electron source 402 is embodied as a thermal field emitter. Electrons emerging from the electron source 402 are accelerated to the anode 404 due to a potential difference between the electron source 402 and the anode 404. Accordingly, a particle beam in the form of an electron beam is formed along a first optical axis OA1.

The particle beam is guided along a beam path, which corresponds to the first optical axis OA1, after the particle beam has emerged from the electron source 402. A first electrostatic lens 405, a second electrostatic lens 406, and a third electrostatic lens 407 are used to guide the particle beam.

Furthermore, the particle beam is adjusted along the beam path using a beam guiding device. The beam guiding device of this exemplary embodiment comprises a source setting unit with two magnetic deflection units 408 arranged along the first optical axis OA1. Moreover, the particle beam apparatus 400 comprises electrostatic beam deflection units. A first electrostatic beam deflection unit 409, which is also embodied as a quadrupole in a further exemplary embodiment, is arranged between the second electrostatic lens 406 and the third electrostatic lens 407. The first electrostatic beam deflection unit 409 is likewise arranged downstream of the magnetic deflection units 408. A first multi-pole unit 409A in the form of a first magnetic deflection unit is arranged at one side of the first electrostatic beam deflection unit 409. Moreover, a second multi-pole unit 409B in the form of a second magnetic deflection unit is arranged at the other side of the first electrostatic beam deflection unit 409. The first electrostatic beam deflection unit 409, the first multi-pole unit 409A, and the second multi-pole unit 409B are set for the purposes of setting the particle beam in respect of the axis of the third electrostatic lens 407 and the entrance window of a beam deflection device 410. The first electrostatic beam deflection unit 409, the first multi-pole unit 409A and the second multi-pole unit 409B may interact like a Wien filter. A further magnetic deflection element 432 is arranged at the entrance to the beam deflection device 410.

The beam deflection device 410 is used as a particle beam deflector, which deflects the particle beam in a specific manner. The beam deflection device 410 comprises a plurality of magnetic sectors, namely a first magnetic sector 411A, a second magnetic sector 411B, a third magnetic sector 411C, a fourth magnetic sector 411D, a fifth magnetic sector 411E, a sixth magnetic sector 411F, and a seventh magnetic sector 411G. The particle beam enters the beam deflection device 410 along the first optical axis OA1 and it is deflected by the beam deflection device 410 in the direction of a second optical axis OA2. The beam deflection is performed by means of the first magnetic sector 411A, by means of the second magnetic sector 411B and by means of the third magnetic sector 411C through an angle of 30° to 120°. The second optical axis OA2 is aligned with the first optical axis OA1 at the same angle. The beam deflection device 410 also deflects the particle beam which is guided along the second optical axis OA2, to be precise in the direction of a third optical axis OA3. The beam deflection is provided by the third magnetic sector 411C, the fourth magnetic sector 411D, and the fifth magnetic sector 411E. In the exemplary embodiment in FIG. 3, the deflection with respect to the second optical axis OA2 and with respect to the third optical axis OA3 is provided by deflecting the particle beam at an angle of 90°. Hence, the third optical axis OA3 extends coaxially with respect to the first optical axis OA1. However, reference is made to the fact that the particle beam apparatus 400 according to the invention described here is not restricted to deflection angles of 90°. Rather, any suitable deflection angle may be selected by the beam deflection device 410, for example 70° or 110°, such that the first optical axis OA1 does not extend coaxially with respect to the third optical axis OA3. In respect of further details of the beam deflection device 410, reference is made to WO 2002/067286 A2.

After the particle beam was deflected by the first magnetic sector 411A, the second magnetic sector 411B, and the third magnetic sector 411C, the particle beam is guided along the second optical axis OA2. The particle beam is guided to an electrostatic mirror 414 and it extends on its path to the electrostatic mirror 414 along a fourth electrostatic lens 415, a third multi-pole unit 416A in the form of a magnetic deflection unit, a second electrostatic beam deflection unit 416, a third electrostatic beam deflection unit 417, and a fourth multi-pole unit 416B in the form of a magnetic deflection unit. The electrostatic mirror 414 comprises a first mirror electrode 413A, a second mirror electrode 413B, and a third mirror electrode 413C. Electrons of the particle beam which are reflected back at the electrostatic mirror 414 once again extend along the second optical axis OA2 and re-enter the beam deflection device 410. Then, they are deflected to the third optical axis OA3 by the third magnetic sector 411C, the fourth magnetic sector 411D, and the fifth magnetic sector 411E.

The electrons of the particle beam emerge from the beam deflection device 410 and are guided along the third optical axis OA3 to the object 425 which is intended to be examined. On the path to the object 425, the particle beam is guided to a fifth electrostatic lens 418, a beam guiding tube 420, a fifth multi-pole unit 418A, a sixth multi-pole unit 418B, and an objective lens 421. The fifth electrostatic lens 418 is an electrostatic immersion lens. By way of the fifth electrostatic lens 418, the particle beam is decelerated or accelerated to an electric potential of the beam guiding tube 420.

By means of the objective lens 421, the particle beam is focused in a focal plane in which the object 425 is arranged. The object 425 is arranged on a movable sample stage 424. The movable sample stage 424 is arranged in a sample chamber 426 of the particle beam apparatus 400.

The objective lens 421 may be embodied as a combination of a magnetic lens 422 and a sixth electrostatic lens 423. The end of the beam guiding tube 420 further may be an electrode of an electrostatic lens. After emerging from the beam guiding tube 420, particles of the particle beam apparatus are decelerated to a potential of the object 425 arranged on the sample stage 424. The objective lens 421 is not restricted to a combination of the magnetic lens 422 and the sixth electrostatic lens 423. Rather, the objective lens 421 may assume any suitable form. By way of example, the objective lens also may be embodied as a purely magnetic lens or as a purely electrostatic lens.

The particle beam which is focused onto the object 425 interacts with the object 425, interaction particles emerging as a result thereof. In particular, secondary electrons are emitted from the object 425 or backscattered electrons are scattered back at the object 425. The secondary electrons or the backscattered electrons are accelerated again and guided into the beam guiding tube 420 along the third optical axis OA3. In particular, the trajectories of the secondary electrons and the backscattered electrons extend on the route of the beam path of the particle beam in the opposite direction to the particle beam.

The particle beam apparatus 400 comprises a first detector 419 which is arranged between the beam deflection device 410 and the objective lens 421 along the beam path. Secondary electrons traveling in directions aligned at a large angle with respect to the third optical axis OA3 are detected by the first detector 419. The first detector 419 is connected to a display unit 603.

Backscattered electrons and secondary electrons which have a small axial distance with respect to the third optical axis OA3 at the location of the first detector 419—i.e. backscattered electrons and secondary electrons which have a small distance from the third optical axis OA3 at the location of the first detector 419—enter the beam deflection device 410 and are deflected to an analysis detector 428 of an analysis device 500 by the fifth magnetic sector 411E, the sixth magnetic sector 411F and the seventh magnetic sector 411G along a detection beam path 427. The analysis device 500 is also connected to the display unit 603 (not depicted here).

The first detector 419 generates detection signals which are largely generated by emitted secondary electrons. The detection signals which are generated by the first detector 419 are guided to the display unit 603 and used to obtain information about the properties of the interaction region of the focused particle beam with the object 425. In particular, the focused particle beam is scanned over the object 425 using a scanning device 429. Then, an image of the scanned region of the object 425 can be generated by the detection signals, which are generated by the first detector 419, and it can be displayed on the display unit 603, for example a monitor.

The analysis device 500 has a retarding field grid device 430 arranged upstream of the analysis detector 428. Then, an image of the scanned region of the object 425 can be generated by the detection signals, which are generated by the analysis device 500, and it can be displayed on the display unit 603.

The particle beam apparatus 400 likewise comprises a processor 600, loaded onto which there is a computer program product with program code which controls the particle beam apparatus 400. This is discussed in more detail further below. The processor 600 is also connected to the control unit 601 in this exemplary embodiment, said control unit comprising a memory unit 602. The control unit 601 serves to actuate at least one guide unit of the particle beam apparatus 400, which guide units were explained above in respect of the description of the particle beam apparatus 400: the first electrostatic lens 405, the second electrostatic lens 406, the third electrostatic lens 407, the magnetic deflection unit 408, the first electrostatic beam deflection unit 409, the first multi-pole unit 409A, the second multi-pole unit 409B, the beam deflection device 410, the first magnetic sector 411A, the second magnetic sector 411B, the third magnetic sector 411C, the fourth magnetic sector 411D, the fifth magnetic sector 411E, the sixth magnetic sector 411F, the seventh magnetic sector 411G, the first mirror electrode 413A, the second mirror electrode 413B, the third mirror electrode 413C, the electrostatic mirror 414, the fourth electrostatic lens 415, the second electrostatic beam deflection unit 416, the third multi-pole unit 416A, the fourth multi-pole unit 416B, the third electrostatic beam deflection unit 417, the fifth electrostatic lens 418, the fifth multi-pole unit 418A, the sixth multi-pole unit 418B, the objective lens 421, the magnetic lens 422 and the sixth electrostatic lens 423. For reasons of clarity, FIG. 3 only depicts that the third mirror electrode 413C is connected to the control unit 601.

A radiation detector 502 with which interaction radiation arising on account of an interaction between the primary electron beam and the object 425 is detected is also arranged in the sample chamber 426. By way of example, the interaction radiation is, once again, x-ray radiation or cathodoluminescence. The radiation detector 502 is likewise connected to the display unit 603.

The sample stage 424 is designed to be movable in three directions arranged perpendicular to one another, namely in an x-direction, in a y-direction and in a z-direction. Additionally, the sample stage 424 may be rotated about a first axis of rotation and about a second axis of rotation arranged perpendicular to the first axis of rotation. It is possible to set the distance WD of the surface of the object 425 from the sixth electrostatic lens 423 by means of a movement of the sample stage 424 in the z-direction, which extends parallel to the optical axis OA3 or corresponds to the latter. This is the working distance. By way of example, it lies in the range from 0.3 mm to 20 mm or in the range from 0.5 mm to 12 mm in this case too. The range limits are included in the predeterminable range. Reference is explicitly made to the fact that the aforementioned distance values should only be understood to be exemplary and not restrictive. Instead, other values for the distance may also be selected.

Now, exemplary embodiments of the method according to the system described herein, which are used in the SEM 100 as per FIG. 1, are described below. Reference is explicitly made to the fact that the exemplary embodiments of the method according to the system described herein may also be used analogously in the combination apparatus 200 in accordance with FIG. 2 or in the particle beam apparatus 400 in accordance with FIG. 3.

Figure 4:
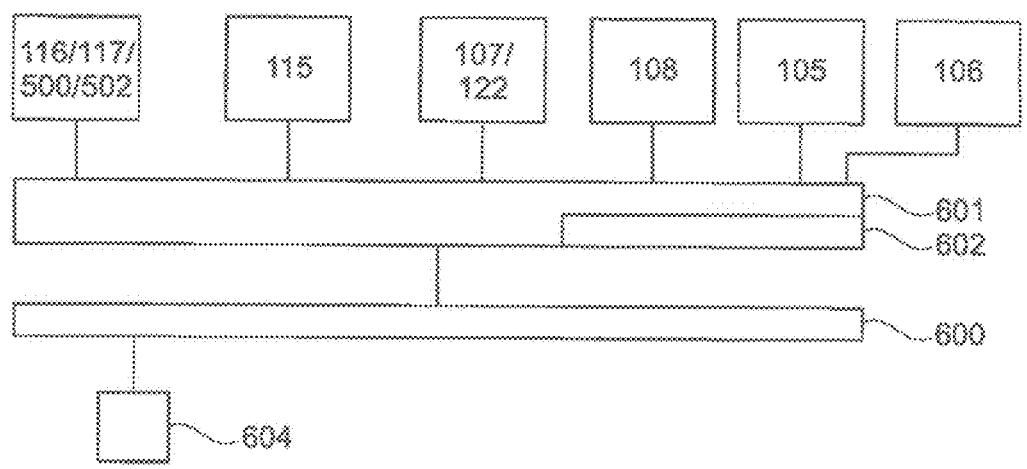
FIG. 4 shows a schematic illustration of units of the particle beam apparatus in accordance with FIG. 1, which units are actuated by a control unit.

FIG. 4 shows a schematic illustration of the units of the SEM 100 which are actuated by the control unit 601. The control unit 601, which comprises the memory unit 602, is firstly connected to the processor 600. The processor 600 in turn is connected to a fundamental parameter control unit 604. The fundamental parameter control unit 604 is used to set values of the landing energy of the electrons or the working distance WD, as will still be explained in more detail below.

By way of example, the control unit 601 serves to set the contrast in the generated image by means of a first control parameter or set the brightness in the generated image by means of a second control parameter. By way of example, a gain factor of an amplifier of at least one of the following detectors is adjusted to this end: the first detector 116, the second detector 117, the analysis device 500 and the radiation detector 502. A voltage at the collector grid 501 of the analysis device 500 may also be set by means of the control unit 601.

Moreover, it is possible to actuate the scanning device 115 by means of the control unit 601. By way of example, the scanning speed, with which the primary electron beam may be scanned over the object 114, is set by actuating the scanning device 115 by means of a third control parameter.

The control device 601 also serves to actuate e.g. the first objective lens 107 by means of a fourth control parameter, with the objective lens 107 setting the focusing of the primary electron beam onto the object 114. Further, the control unit 601 may also be used to set the electrostatic and/or magnetic units of the SEM 100, with the electrostatic and/or magnetic units being labeled by reference sign 122 in FIG. 4. By way of example, the primary electron beam is centered in the first objective lens 107 by setting the electrostatic and/or magnetic units 122 by means of a fifth control parameter. Moreover, the electrostatic and/or magnetic deflection units 122 may be actuated by means of a sixth control parameter in such a way that there is a "beam shift" in the SEM 100.

Moreover, the control unit 601 also serves to set the position of a mechanically displaceable unit of the SEM 100 by means of a seventh control parameter. By way of example, the first aperture unit 108 has a mechanically displaceable embodiment.

Further, the control unit 601 also serves to set the condenser lens 105 by means of an eighth control parameter and/or to set the stigmator 106 by means of a ninth control parameter.

Figure 5:
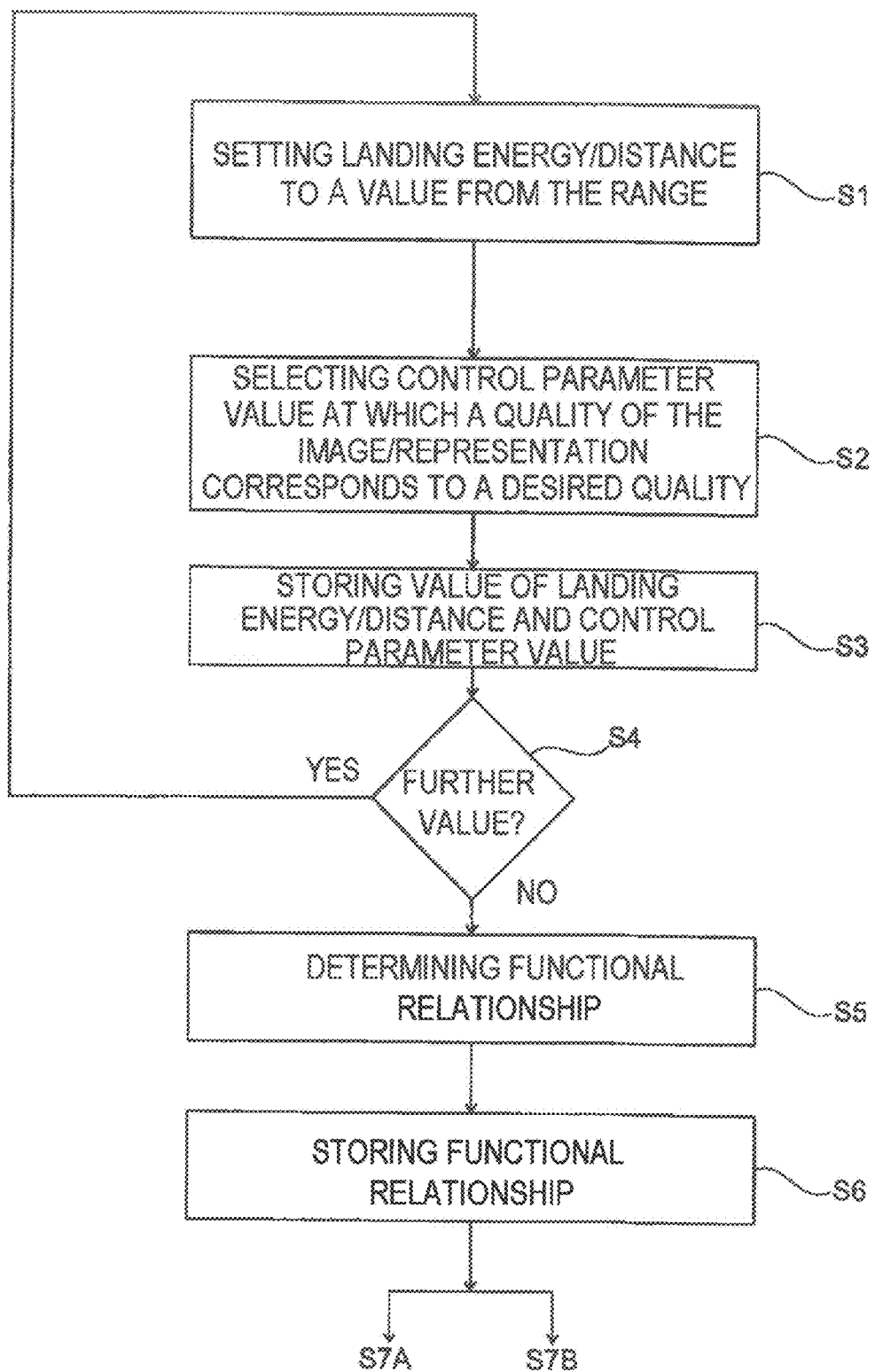
FIG. 5 shows a flowchart of a first part of a method for generating images of an object and/or representations of data about the object.

FIG. 5 schematically shows a flowchart of a first part of the method according to the system described herein. In method step S1, the landing energy is set to a first value from a predeterminable range of the landing energy of the electrons or the working distance WD is set by moving the sample carrier 503. By way of example, setting is carried out using the fundamental parameter control unit 604 (cf. FIG. 4).

The landing energy of the electrons corresponds to the energy with which the object 114 is examined and/or imaged. As described above in respect of the electrostatic retardation device of the SEM 100, the landing energy of the electrons may differ from the energy with which the electrons of the primary electron beam are guided through the beam guiding tube 104 of the SEM 100. Rather, provision is made for initially accelerating the electrons very strongly and only decelerating the latter to the landing energy just before incidence on the object 114. By way of example, the predeterminable range of the landing energy lies between 1 eV and 30 keV, including the range boundaries. However, the predeterminable range of the landing energy of the electrons is not restricted to these values. Rather, the predeterminable range may include any suitable value which is suitable for the system described herein.

In the case where the distance is set between the beam guiding tube 104 of the SEM 100 and the surface region of the object 114, the predeterminable range is e.g. from 0.3 mm to 20 mm or from 0.5 mm to 12 mm. The range limits are included in the predeterminable range. Reference is explicitly made to the fact that the aforementioned distance values should only be understood to be exemplary and not restrictive. Instead, other values for the distance may also be selected.

If the landing energy was set in method step S1, then the landing energy, but not, however, the distance, is optionally set to further values in the further method steps. However, if the distance was set in method step S1, then the distance, but not, however, the landing energy, is optionally set to further values in the further method steps. Both variants (i.e. setting the landing energy on the one hand and setting the distance on the other hand) are referred to as method according to the system described herein, below.

In a first embodiment, a first control parameter value of at least one control parameter from the set of the first control parameter to the ninth control parameter is now set at or using the control unit 601 in method step S2. If the first control parameter value of this control parameter is used, a first image of the object 114 is obtained with a desired image quality and/or a first desired representation of data about the object 114. By way of example, the control parameter is a physical variable, in particular a control current or a control voltage, but also e.g. the ratio of physical variables, in particular an amplification of physical variables. The values of the physical variables are adjustable at the control unit or using the control unit 601 and these control and/or feed one of the aforementioned units of the SEM 100 in such a way that desired physical effects, for example, the generation of specific magnetic fields and/or electrostatic fields, are brought about.

If an image of the object 114 is created, then the first control parameter value of the control parameter is selected in such a way that the image of the object 114 is created with such a good image quality that a user is able to analyze the object 114 to be examined well on account of the image and the image information contained therein. Here, the image quality may be determined by means of e.g. objective criteria. By way of example, the image quality of an image becomes better with increasing resolution in the image. Alternatively, the image quality may be determined on the basis of subjective criteria. Here, a user determines individually as to whether or not an obtained image quality is sufficient. However, what may by all means occur in this case is that the image quality deemed sufficient by a first user is not considered sufficient by a second user. In respect of determining the image quality, reference is also made to the remarks further above, which are likewise explicitly referred to here.

As explained, provision is additionally or alternatively made for the first control parameter value of the control parameter to be selected in such a way that a desired representation of data about the object 114 (in particular a radiation spectrum, for example an x-ray spectrum) is obtained. The desired representation has a desired quality. In respect of determining the quality of the representation, reference is also made to the remarks further above, which are likewise explicitly referred to here.

In a second embodiment of the method according to the system described herein, provision is made in method step S2 for not only a single first control parameter value of a control parameter to be set for a single unit of the SEM 100, but rather for a plurality of first control parameter values of in each case different control parameters to be set for in each case different units of the SEM 100. By way of example, provision is made for a first control parameter value to be set in each case for each one of the first control parameter to the ninth control parameter until the desired image quality and/or the desired representation of data about the object 114 is/are obtained.

The set value of the landing energy or the set value of the distance and the set first control parameter value are stored in the memory unit 602 in a further method step S3. If the further embodiment of the method according to the system described herein is carried out, the set value of the landing energy or of the distance and all set first control parameter values of the first control parameter to the ninth control parameter are stored in the memory unit 602.

Whether a further image and/or a further representation should be recorded is ascertained in a further method step S4. If so, method steps S1 to S3 are repeated. In the first embodiment of the method, the landing energy is set to a second value from the predeterminable range of the landing energy or the distance is set to a second value from the predeterminable range of the distance in method step S1. Further, a second control parameter value of the control parameter, in the case of which a second image of the object 114 with the desired image quality and/or a second desired representation of data about the object 114 is/are obtained, is then set at or using the control unit 601 in method step S2. In particular, the desired image quality comprises the contrast desired by a user. In the second embodiment of the method according to the system described herein, provision is made in method step S2 for a plurality of second control parameter values for a plurality of the first control parameter to the ninth control parameter to be set for the in each case different units of the SEM 100. By way of example, provision is made for a second control parameter value to be set in each case for each one of the first control parameter to the ninth control parameter until the desired image quality and/or the desired representation of data about the object 114 is/are obtained.

In the first embodiment, the set value of the landing energy or of the distance and the selected second control parameter value are stored in the memory unit 602 in method step S3. If the second embodiment of the method according to the system described herein is carried out, the set value of the landing energy or of the distance and all set second control parameter values of the first control parameter to the ninth control parameter are stored in the memory unit 602.

If no further value of the landing energy or of the distance is intended to be set in method step S4, method step S5 follows. Now, a functional relationship between the set control parameter values of each set control parameter is determined in method step S5 depending on the predeterminable range of the landing energy or of the distance.

Figure 8:
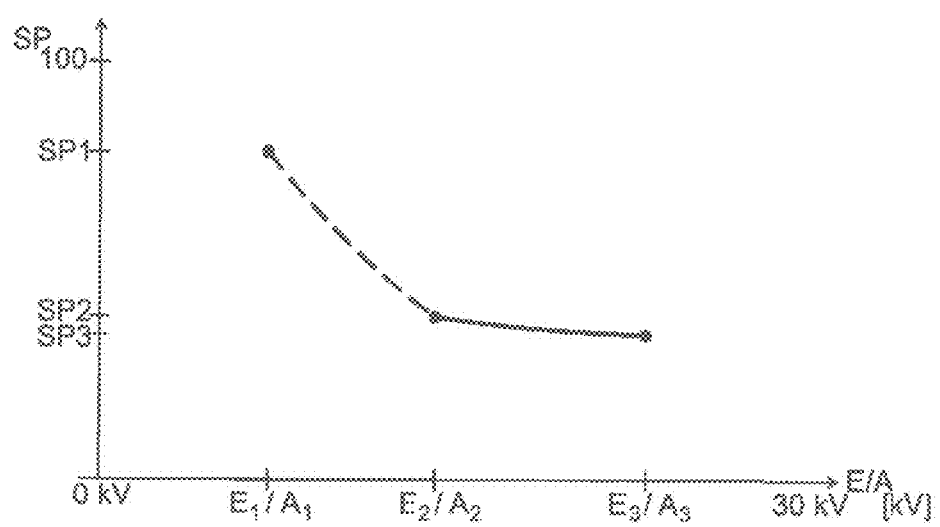
FIG. 8 shows a schematic illustration of the dependence of a control parameter on the landing energy of a particle beam or on a distance of an object from the beam column of a particle beam apparatus.

This is now explained on the basis of FIG. 8. FIG. 8 shows the dependence of a single control parameter SP of a single settable unit of the SEM 100, which units were explained in respect of the first control parameter to the ninth control parameter, depending on the landing energy E or on the distance A. Three images with a sufficiently good image quality and/or three desired representations of data about the object 114 were determined in the exemplary embodiment in accordance with FIG. 8. Accordingly, method steps S1 to S3 were carried out a total of three times. A first control parameter value SP1 of a control parameter SP was selected for a first value E1 of the landing energy E (or for a first value A1 of the distance A) for a first image having a sufficiently good image quality and/or for a first desired representation of data about the object 114. Further, a second control parameter value SP2 of the control parameter SP was selected for a second value E2 of the landing energy E (or for a second value A2 of the distance A) for a second image having a sufficiently good image quality and/or for a second desired representation of data about the object 114. Moreover, a third control parameter value SP3 of the control parameter SP was selected for a third value E3 of the landing energy E (or for a third value A3 of the distance A) for a third image having a sufficiently good image quality and/or for a third desired representation of data about the object 114.

Now, a functional relationship is ascertained between the first control parameter value SP1, the second control parameter value SP2 and the third control parameter value SP3 depending on the predeterminable range of the landing energy E (or of the distance A). The functional relationship may be a linear relationship or a nonlinear relationship. A step function may by all means also be comprised by the functional relationship or form the functional relationship. By way of example, the functional relationship may be determined by an interpolation. Any suitable interpolation method, for example a linear interpolation, a nonlinear interpolation, a trigonometric interpolation, a logarithmic interpolation and/or a spline interpolation, may be used in the interpolation. In addition and/or as an alternative thereto, provision is made for determining the functional relationship by extrapolation. Any suitable extrapolation method, for example a linear extrapolation, a nonlinear extrapolation, a trigonometric extrapolation and/or a logarithmic extrapolation, may be used in the extrapolation. As an alternative or in addition thereto, the functional relationship may be determined by forming an average, ascertaining random values and/or determining the smallest value or the largest value from the set of the first value and the second value.

The functional relationship is determined for each one of the first to ninth control parameters SP depending on the landing energy E or the distance A in a manner analogous to the determination explained using FIG. 8. The determined functional relationship or the determined functional relationships is/are stored in the memory unit 602 in method step S6 (cf. FIG. 5).

Following this, a second part of the method according to the system described herein is carried out, with two exemplary embodiments of the second part of the method according to the system described herein being explained below.

Figure 6:
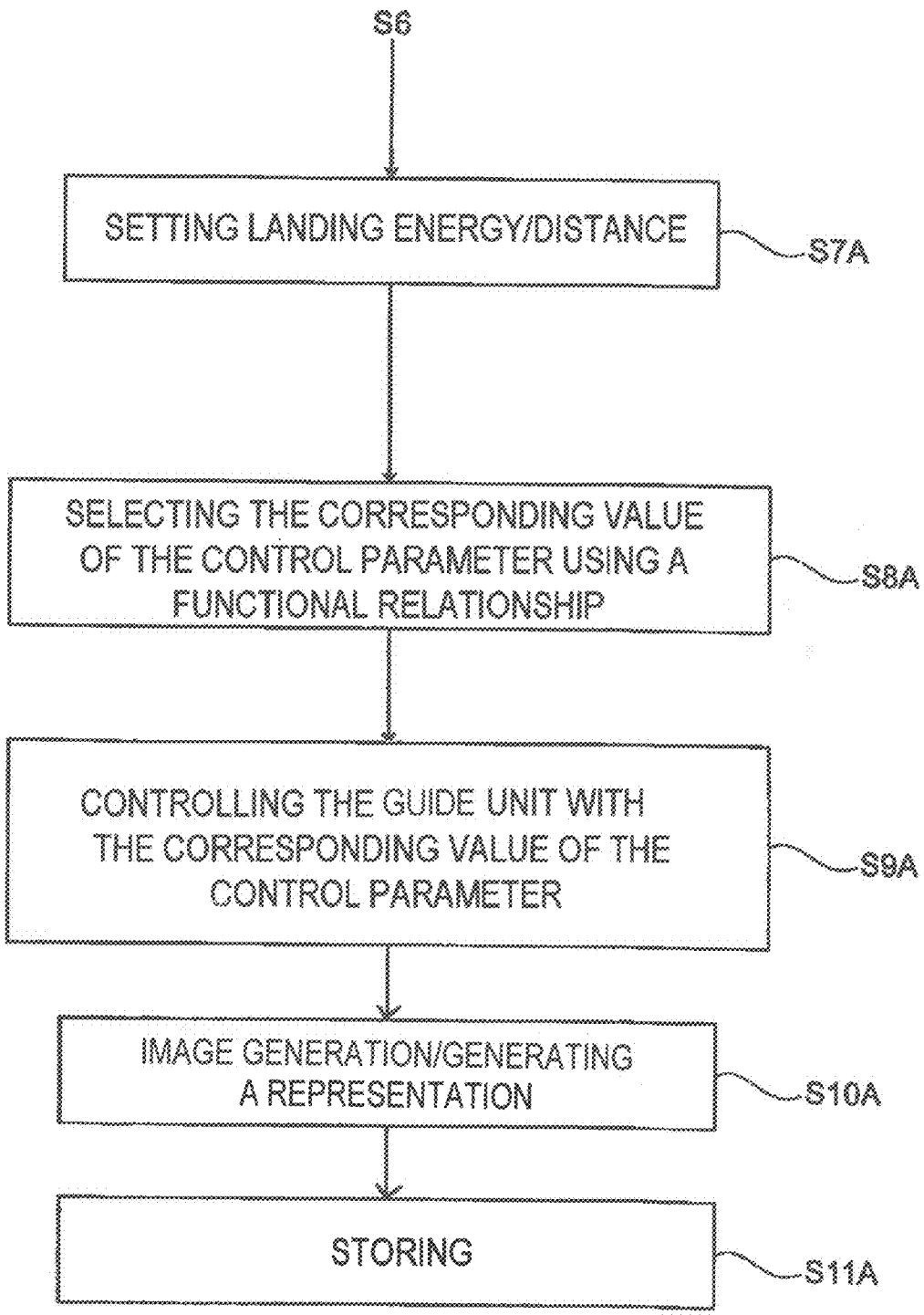
FIG. 6 shows a flowchart of an exemplary embodiment of a second part of the method according to FIG. 5.

Method steps S7A to S11A are carried out in a first exemplary embodiment of the second part of the method according to the system described herein. Method steps S7A to S11A are depicted in FIG. 6. A desired value of the landing energy or of the distance is set in method step S7A.

Thus, accordingly, there is either setting of a desired value of the landing energy of the electrons of the primary electron beam, with which the object 114 should be examined and/or imaged, or setting of a desired value of the distance already explained above. This desired value lies in the respective predeterminable range and, as a rule, is not any of the values which were already set in the method explained further above. The predeterminable ranges of the landing energy and of the distance have already been explained further above.

The corresponding value of the control parameter, which is set at or using the control unit 601, is determined on the basis of the determined functional relationship in method step S8A. By way of example, determining is carried out for each one of the control parameters which were taken into account in the first part of the method according to the system described herein, i.e., for example, for the first control parameter to the ninth control parameter. The control unit 601 is then used to actuate each settable unit with the corresponding value of the respective control parameter associated therewith in a further method step S9A.

If the image/data quality determined by the functional relationship at the selected work point of method step S7A (i.e. the set landing energy or the set distance) does not suffice, it may be improved in accordance with method step S2 and likewise be stored in accordance with method step S3. This setting of the ideal image/data quality is simplified since a setting which lies close to the ideal setting has already been ascertained in method step S9A on account of the setting process already carried out. Hence, the adjustment outlay at such a work point is less than in the prior art.

The newly set value is then used for all further determinations of the functional relationship (e.g. in method step S8A). This ensures that the image quality at the work point of method step S7A and in the surroundings thereof was improved. This procedure may be iterative such that an ever-increasing image quality with ever-decreasing adjustment outlay may be obtained in an interval on the basis of previous settings S9A.

Then, the image is generated by detecting interaction particles and/or interaction radiation in a further method step S10A, as already described further above. In addition or as an alternative thereto, a representation of data about the object 114, for example an x-ray spectrum, is generated by detecting interaction radiation. Here too, reference is made to the remarks further above.

In an alternative embodiment, the aforementioned determination is not carried out for each control parameter but only for individual control parameters or for a plurality of control parameters. This is followed by the further steps in a manner analogous to the steps explained above.

In this embodiment, the generated image and/or the generated representation is stored in the memory unit 602 in method step S11A.

Figure 7:
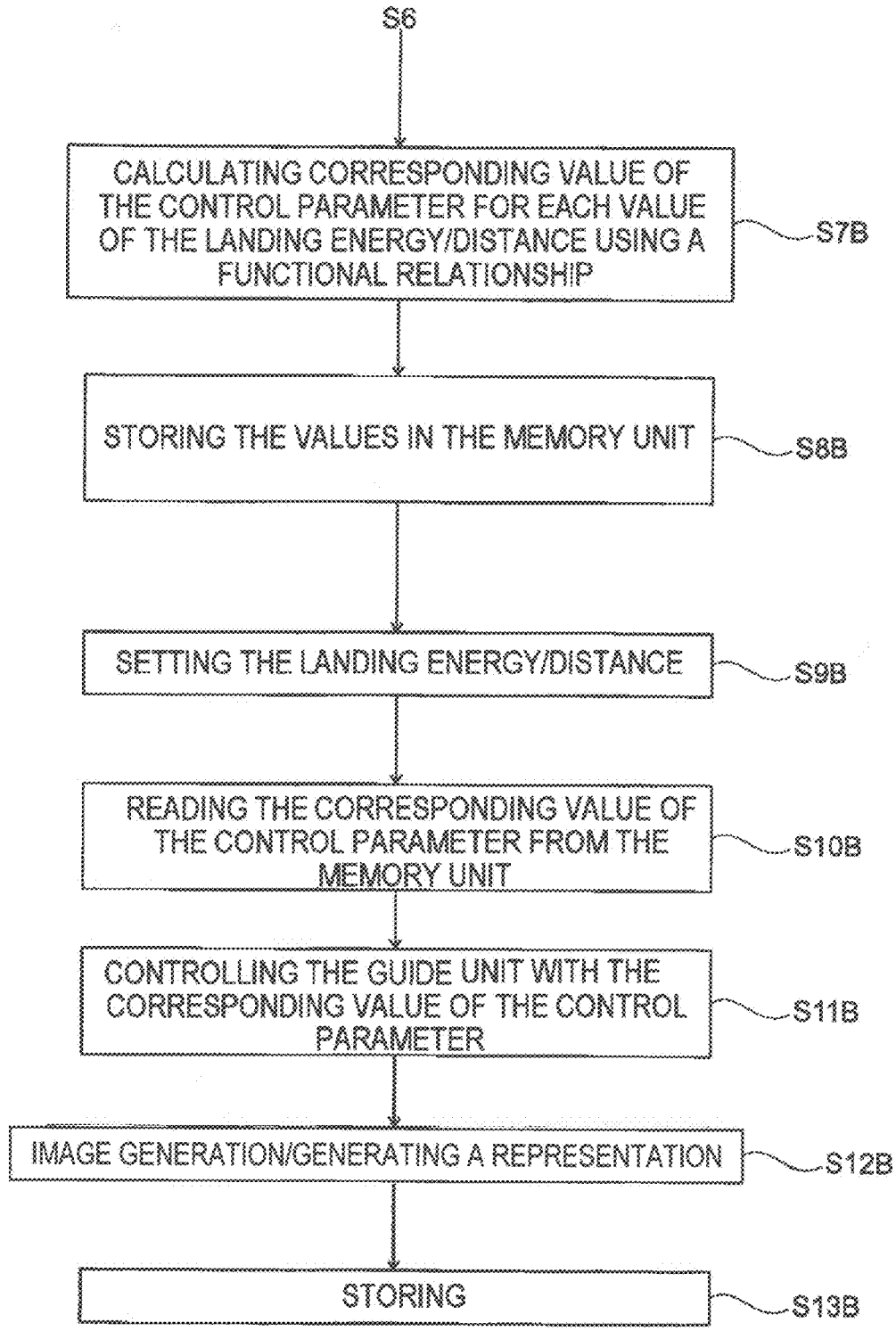
FIG. 7 shows a flowchart of a further exemplary embodiment of a second part of the method according to FIG. 5.

FIG. 7 shows a second exemplary embodiment of the second part of the method according to the system described herein, comprising method steps S7B to S13B, which may be carried out after method step S6. This exemplary embodiment is based on the idea of initially calculating and subsequently storing the corresponding value of each of the first control parameter to the ninth control parameter for each possible value of the landing energy of the electrons or of the aforementioned distance. Then, each corresponding value of the respective control parameter is readable from the memory unit 602 when a desired value of the landing energy or of the distance is set. Therefore, the corresponding value of each of the first control parameter to the ninth control parameter is calculated with the aid of the determined functional relationship for each value of the landing energy or of the distance from the respective predeterminable range in method step S7B in this exemplary embodiment. Each calculated corresponding value of each of the first control parameter to the ninth control parameter is then stored in the memory unit 602 in method step S8B, together with the respective value of the landing energy or of the distance. In principle, number tuples are stored in the memory unit 602, with each tuple having a value of the landing energy and all corresponding values of the first control parameter to the ninth control parameter which were taken into account in the first part of the method according to the system described herein. When the distance is set, number tuples are stored in the memory unit 602, with each tuple having a value of the distance and all corresponding values of the first control parameter to the ninth control parameter which were taken into account in the first part of the method according to the system described herein.

If a user now sets a certain desired value of the landing energy or of the aforementioned distance in method step S9B, the values of the first control parameter to the ninth control parameter corresponding to this set desired value are read out of the memory unit 602 in method step S10B. The aforementioned units of the SEM 100 are actuated by the corresponding associated and read corresponding values of the control parameters in method step S11B. Then, an image is generated by detecting interaction particles and/or interaction radiation in method step S12B, as already described above. In addition or as an alternative thereto, a representation of data about the object 114, for example an x-ray spectrum, is generated by detecting interaction radiation. Here too, reference is made to the remarks further above.

In this embodiment, the generated image and/or the generated representation is stored in the memory unit 602 in method step S13B.

Now, the landing energy/distance may also be set in an automated fashion in method step S9B (in contrast to method step S7A). By way of example, it is now possible to fix values in an interval of the landing energy values/ distances in advance, at which method steps S9B-S13B are carried out in each case, without the presence of a user being required.

The method according to the system described herein renders it possible to determine a functional relationship between the values of the control parameter (or the control parameters) and the landing energy or the distance by recording a few images, which each have a sufficient desired image quality, and by determining the values of the control parameter (or the control parameters) leading to these images and the landing energy or the aforementioned distance. Additionally or alternatively, the method according to the system described herein renders it possible to determine a functional relationship between the values of the control parameter (or the control parameters) and the landing energy or the distance by generating a few representations of data about the object, which each have a sufficient desired quality, and by determining the values of the control parameter (or the control parameters) leading to these representations and the landing energy or the aforementioned distance. As a result of this functional relationship, it is then possible to calculate the associated control parameter value for each landing energy or for each distance in order to obtain the desired image quality in the image and/or quality of the representation of data about the object. Using the method according to the system described herein, it is possible to obtain a desired image quality in the image and/or quality of the representation of data about the object much more quickly than with the methods known from the prior art. Also, in particular, it is possible, in an automated fashion, to record numerous images or representations of data about the object at different values of the landing energy or of the distance with the corresponding values of the control parameters such that a sufficiently good image quality in all images and/or quality of the representation of data about the object is/are obtained at all times.

Special applications are described below in an exemplary manner.

Figure 9:
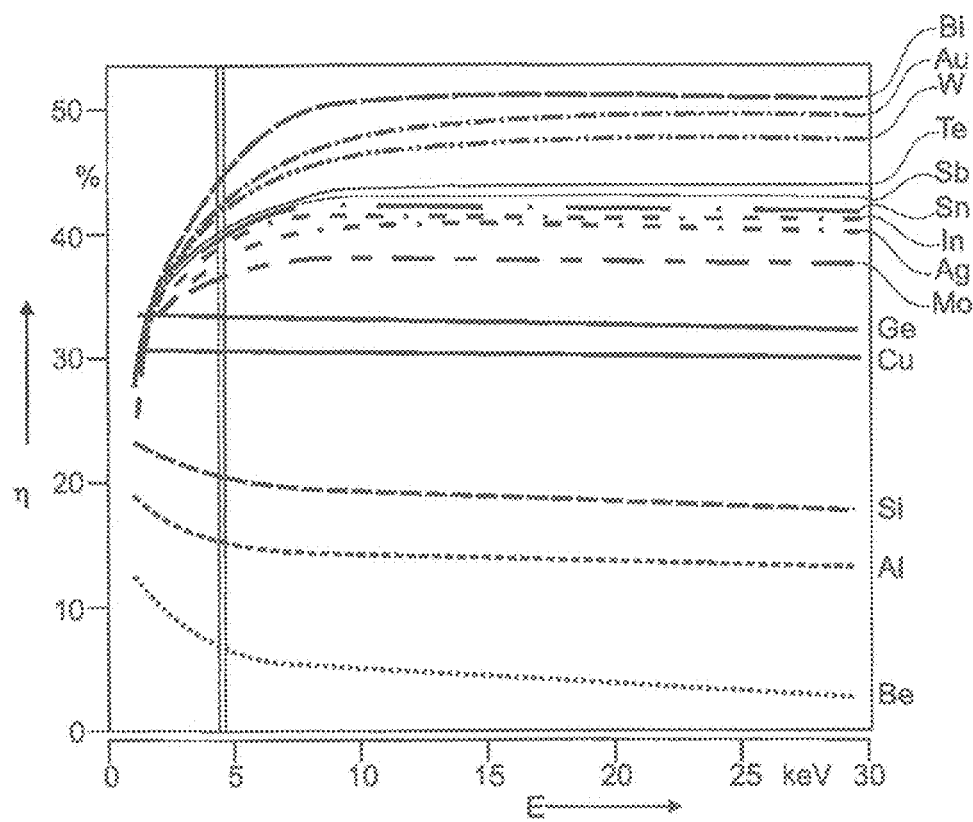
FIG. 9 shows a schematic illustration of the dependence of the backscatter coefficient on the landing energy of a particle beam.

Using the method according to the system described herein, it is possible to determine a so-called contrast reversal which then facilitates deductions about the material composition of the object to be examined. Below, the contrast reversal is explained on the basis of backscattered electrons. As FIG. 9 shows schematically, the backscatter coefficients η of the backscattered electrons are dependent, firstly, on the material of the object to be examined and, secondly, on the landing energy E of the charged particles, with which the object is examined and imaged (adopted from "LVSEM" according to L. Reimer, 1995). Essentially, it is possible to state that, in the region of 5 keV, the backscatter coefficients for materials increase monotonically with increasing atomic number Z. At a lower landing energy, i.e. at energies of less than 5 keV, the backscatter coefficient curves of the various elements intersect with decreasing landing energy. This means that the contrast increases monotonically with increasing atomic number Z at a high landing energy. When the landing energy reduces, it is possible to find backscatter coefficients such that—depending on the atomic number of the material—there may be a contrast reversal at specific landing energy values. A previously bright image region turns into a dark image region or a previously dark image region now turns into a bright image region. By means of the method according to the system described herein, it is now possible, firstly, to quickly pass through the entire energy range and record images for each desired energy. This may also be carried out automatically, and so a user need not be present when the images are recorded. On account of knowledge about the approximate profile of the backscatter coefficients and on account of the contrast reversal, it is then e.g. easily possible to identify materials.

In a further embodiment of the system described herein, provision is made for determining the contrast reversal by sequential observation of images which e.g. were recorded for specific landing energy values (e.g. landing energy values E1 to E10) with the different detectors. The landing energy values E1 to E10 differ from one another. The landing energy values E1 to E10 delimit an energy range. The landing energy values E2 to E9 are contained in this energy range.

Initially, images are recorded by the different detectors at each one of the landing energy values E1 to E10. By way of example, a first image is recorded with the first detector 116, a second image is recorded with the second detector 117 and a third image is recorded with the analysis device 500 at the landing energy E1, with the aforementioned images being recorded simultaneously by the aforementioned detectors. Then, a fourth image is recorded with the first detector 116, a fifth image is recorded with the second detector 117 and a sixth image is recorded with the analysis device 500 at the landing energy E2, with the aforementioned images being recorded simultaneously by the aforementioned detectors in this case too. The procedure above is then also undertaken in analogous fashion for the further determined landing energy values E3 to E10.

In the case of identical landing energy values E, the different detectors arranged at different locations in the SEM 100 generate images with a different contrast in each case. This is linked to the fact that the quantitative generation of secondary electrons and backscattered electrons depends on the landing energy E. The angular distribution of the secondary electrons and backscattered electrons (i.e. the region in which the secondary electrons and backscattered electrons extend from the object 114 to be examined in the direction of the beam guiding tube 104) also depends on the landing energy E. Detectors which primarily detect secondary electrons (e.g. the second detector 117 and the analysis device 500 and the first detector 116 without use of the retarding field grid 116A) generate images in which the contrast is mainly determined by the topography of the surface (also referred to as topography contrast). By contrast, detectors which mainly detect backscattered electrons (e.g. the first detector 116 using the retarding field grid 116A for filtering out the secondary electrons) generate images, the contrast of which is mainly determined by the material of the object 114 (also referred to as material contrast). On account of the fact that the images recorded by the different detectors have a different contrast, a contrast reversal for an identical region of the object 114 at different landing energy values can be identified quite quickly. By way of example, a contrast reversal may already be visible between the image of the first detector 116 at the landing energy E3 and the image of the first detector 116 at the landing energy E4, while the images of the detectors referred to further above of the SEM 100 do not yet exhibit a contrast reversal. Hence, it is now possible to determine a contrast reversal relatively quickly. In this way, information about the landing energy values E at which a contrast reversal occurs is obtained relatively quickly and it is then possible, for example on account of the known relationship between the landing energy and the backscatter coefficient already explained above, to deduce the material composition of the region of the object 114 at which the contrast reversal takes place.

By way of example, provision is made for ascertaining whether a contrast reversal has occurred in one of the images at two different landing energy values E, either after or still during the recording of the images using the aforementioned detectors.

In a further exemplary embodiment of the method according to the system described herein, provision is made for determining the landing energy E, at which the contrast reversal occurs, more closely. This is elucidated below using an example. Below, the assumption is made that a contrast reversal occurs at the first detector 116 between the landing energy values E3 and E4. Then, the range of the landing energy values between E3 and E4 is passed over again. Expressed differently, starting from E3, images are recorded with the first detector 116 at an energy interval which is smaller than the difference between E3 and E4. Here, the landing energy is increased step-by-step by the energy interval after each recording of an image until the landing energy E4 has been reached. Subsequently, the images which were recorded with the landing energy values between E3 and E4 are considered and the contrast reversal point is determined.

In a further application of the system described herein, provision is made for the images, in each case recorded at a very specific landing energy E or at a very specific working distance WD, of at least two of the aforementioned detectors to be combined with one another in order to highlight specific contrasts which emerge on account of interaction processes within the object or on account of the different detection types. Here, the images of at least two detectors, preferably of all detectors, are linked with one another by a mathematical function:

$$f_{Linked} = f_{Detector\ i} OP\ f_{Detector\ i+1} OP \ldots OP\ f_{Detector\ n-1} OP\ f_{Detector\ n} \quad [3]$$

where:
$f_{Linked}$ is the obtained image signal after linking,
$f_{Detector\ i}$ is the detector signal of the i-th detector,
i is an integer between 1 and n, and
OP is any mathematical operator.

In an even further application of the system described herein, provision is made for the images, in each case recorded at different landing energy values E or at different working distances WD, of a single detector to be combined with one another in order to highlight specific contrasts which emerge on account of interaction processes within the object or on account of the different detection types. Here, the images of this detector are linked to one another by a mathematical function:

$$f_{Linked} = f_{image\ i} OP\ f_{image\ i+1} OP \ldots OP\ f_{image\ n-1} OP\ f_{image\ n} \quad [4]$$

where in this case:
$f_{Linked}$ is the obtained image signal after linking,
$f_{image\ i}$ is the detector signal of the i-th image of the detector, i.e. at an i-th energy value or an i-th distance,
i is an integer between 1 and n, and
OP is any mathematical operator.

In a once again further application of the system described herein, provision is made for the images, in each case recorded at different landing energy values E or at different working distances WD, of at least two of the aforementioned detectors to be combined with one another in order to highlight specific contrasts which emerge on account of interaction processes within the object or on account of the different detection types. Here, the images of at least two detectors, preferably of all detectors, are linked with one another by a mathematical function:

$$f_{Linked} = f_{Detector\ i} OP\ f_{Detector\ i+1} OP \ldots OP\ f_{Detector\ n-1} OP\ f_{Detector\ n} \quad [5]$$

where:
$f_{Linked}$ is the obtained image signal after linking,
$f_{Detector\ i}$ is the detector signal of the i-th detector, generated at any landing energy E or at any working distance WD,
i is an integer between 1 and n, and
OP is any mathematical operator.

The above-described method is an interactive and, at the same time, iterative method:

In a first step, the user sets first values for a set of control parameters of the particle beam apparatus in this way, until he obtains an image he considers satisfactory or satisfactory measurement values. As described above, the assessment of the quality of the image or of the measurement values may be carried out either on the basis of objective criteria or on the basis of subjective criteria. Here, the first values for the set of control parameters may be set by the user proceeding from value combinations of the control parameters obtained during a calibration of the particle beam apparatus and stored in a memory of the controller of the particle beam apparatus. Proceeding from these stored values for the control parameters, the user may set the first values for the set of control parameters by manually changing individual values. Here, in particular, the landing energy of the primary particles, the working distance between the objective of the particle beam apparatus and the object surface, the magnification, the tilt angle between the particle beam and the surface of the object or settings of correction elements for correcting aberrations, in particular geometric aberrations such as the spherical aberration Cs or aberrations Cc depending on the energy of the primary particles, with which the primary particle beam is incident on the object surface, may be considered as control parameters.

When the user is satisfied with the set image quality or with the quality of the measurement values, the user triggers storage of these first values for the set of control parameters. This is one of the steps requiring a user interaction.

In a second step, the user sets second values for the same set of control parameters of the particle beam apparatus in this way, until, once again, he obtains an image he considers satisfactory or satisfactory measurement values. This second set of values for the control parameters may differ from the first values of the set of control parameters by one or more values. By way of example, the second value for the landing energy, for the working distance, for the magnification, for the tilt angle between the particle beam and the surface of the object or in respect of the setting of correction elements for correcting geometric or energy-dependent aberrations may differ from the corresponding first value of the set of control parameters. As described above, the assessment of the quality of the image or of the measurement values may be carried out, once again, either on the basis of objective criteria or on the basis of subjective criteria. Here, the second values for the set of control parameters may be set, once again, by the user proceeding from value combinations of the control parameters obtained during a calibration of the particle beam apparatus and stored in the memory of the controller of the particle beam apparatus. Proceeding from these stored values for the control parameters, the user may set the second values for the set of control parameters by manually changing individual values.

When the user is once again satisfied with the set image quality or with the quality of the measurement values, the user triggers further storage of these second values for the set of control parameters. This is a further step requiring a user interaction.

There may then be a first determination of the functional relationships between the values for the set of control parameters by the controller of the particle beam apparatus on the basis of the first values and the second values for the set of control parameters. A linear relationship usually forms the basis of a functional relationship between the first values and the second values if only two sets of values are available. If the control parameters are denoted by $A_i(S)$, where the index i in each case identifies one of the aforementioned control parameters and S denotes the system setting at which the control parameters are stored, i.e., in the exemplary case above, S1 denotes the system setting at which the first set of control parameters are stored and S2 denotes the system setting at which the second set of control parameters are stored, then a functional relationship of the for $A_i(s) = A_i(S1) + (A_i(S2) - A_i(S1))\ s$ underlies each control parameter in the simplest case of linear functional relationships of the control parameters on a parameter s. As is possible to identify, these linear relationships reproduce the settings of the control parameters of the first set of control parameters for s=0 and the settings of the control parameters of the second set of control parameters at s=1. An interpolation of the control parameters between the values of the first set of control parameters and the second set of control parameters emerges for values of the parameters in the interval [0, 1]. Extrapolations of the control parameters from the first set of control parameters and the second set of control parameters emerge for values of the parameter s<0 and for values for the parameter s>1.

However, instead of the above-described linear functional relationships, nonlinear functional relationships may also underlie this, in particular if nonlinear relationships are to be expected on account of physical laws, such as e.g. between the objective focal lengths of a magnetic objective lens, which should typically be modified when the working distance is changed, and the lens current required to obtain the corresponding objective focal length.

If the user subsequently sets forced coupling between the control parameters, the values for the set of control parameters are subsequently changed on the basis of the discovered functional relationships. If the user subsequently manually changes the value of a control parameter to a third value, the set values of the other control parameters are automatically likewise set to third values in accordance with the functional relationships determined previously. By way of example, the value of the parameter s associated with the third value set by the user is determined by the controller of the particle beam apparatus and inserted into the above equations $A_i(s)=A_i(S1)+(A_i(S2)-A_i(S1))$ s for all other control parameters. To the extent that the third value of the control parameter manually modified by the user lies between the first value and the second value associated with this control parameter, this corresponds to an interpolation between the first and second values. To the extent that the third value of the control parameter manually modified by the user lies outside of the interval between the first value and the second value associated with this control parameter, this corresponds to an extrapolation of the first and second values on the basis of the previously determined functional relationships.

The set forced coupling may be lifted again by the user for the purposes of further fine-tuning. Here, the values for the set of control parameters set previously on the basis of the functional relationships are initially maintained. Proceeding from these values, the user then is once again able to set fourth values for the set of control parameters manually until he once again obtains a satisfactory image or a satisfactory quality of measurement values. When the user is once again satisfied with the set image quality or with the quality of the measurement values, the user may trigger further storage of these fourth values for the set of control parameters.

Then, there subsequently is renewed determination of the functional relationships between the values for the set of control parameters by the controller of the particle beam apparatus on the basis of the first values, the second values and the fourth values for the set of control parameters. Since three values are now available for each control parameter, the functional relationships are now typically determined on the basis of quadratic or cubic splines, the free values of which are in each case determined in such a way that these values are in each case reproduced at the nodes defined by the first values, the second values and the fourth values for the set of control parameters. If the user subsequently turns the forced coupling between the control parameters on again, the values for the set of control parameters are subsequently changed on the basis of the re-determined functional relationships. If the user subsequently manually changes the value of a control parameter to a fifth value, the set values of the other control parameters are automatically likewise set to fifth values in accordance with the functional relationships once again determined previously. The method described above, in which functional relationships between the values of the set of control parameters are iteratively improved with the aid of user interactions, may subsequently be repeated for as long as the user considers this expedient.

As already described further above on the basis of specific examples for the working distance and the landing energy, the functional relationships determined previously may be used to carry out a series of images of the object or of measurement values at the object with reduced user interactions. To this end, the user may select a control parameter and specify the increment with which this control parameter should be modified over which interval. After subsequent triggering of the series function, the controller of the particle beam apparatus subsequently sets the selected control parameter to a value within the interval and selects the values for all other control parameters on the basis of the functional relationships between the control parameters determined previously. After all control parameters have been accordingly set automatically by the controller, there is automatic scanning of the object surface with the particle beam and recording and storing of an image of the object or of the desired measurement values at the object. Subsequently, the controller of the particle beam apparatus automatically changes the selected control parameter to the next value within the interval defined by the user in accordance with the increment defined by the user and automatically likewise sets the associated values for all other control parameters on the basis of the previously determined functional relationships between the control parameters. After all control parameters have been accordingly set, there is renewed automatic scanning of the object surface with the particle beam and recording and storing of a new image of the object or of the desired measurement values at the object. This method is repeated by the controller of the particle beam apparatus until images or measurement values are present for all values of the selected control parameter in the interval defined by the user and with the increment defined by the user. To this end, no user interaction is required while the series function is carried out. After the series function is complete, the user may evaluate image and/or measurement value information obtained while the series function was carried out. Alternatively, the user may also start with the evaluation of the image and/or measurement information obtained while the series function is carried out while the series function is still running. Furthermore, the user is able to abort the series function if he identifies that the quality of the image data or measurement data to be expected with the aid of the series function will not meet his requirements, contrary to his preceding assumptions.

By way of example, the following may be carried out if the user wishes to carry out an examination of an object depending on the landing energy, for example in order to determine the landing energy at which a contrast reversal occurs in the material contrast of his object, but he only knows the approximate energy range (e.g. 1 kV to 5 kV) within which the contrast reversal should occur:

Initially, the user adjusts the particle beam apparatus at a landing energy of 1 keV in such a way that, subjectively, the best image for him is generated. By way of example, he may use the following parameters to this end:

Landing energy=1 keV=$A_1(S1)$

Beam shift $x$=20%=$A_2(S1)$

Beam shift $y$=−40%=$A_3(S1)$

Lens current in the objective lens=1050 mA=$A_4(S1)$

Stigmator $x=-10\%=A_5(S1)$

Stigmator $y=20\%=A_6(S1)$

Contrast detector 1=30%=$A_7(S1)$

Contrast detector 2=20%=$A_8(S1)$

All of the control parameters, such as e.g. the working distance, should remain unchanged in this example and are therefore not specified in this example. The aforementioned set of control parameters $A_i(S1)$, with i=1, 2, . . . 8, for a landing energy of 1 keV is stored, optionally with further control parameters which are not intended to be modified.

Then, the user once again adjusts the particle beam apparatus at a landing energy of 5 keV in such a way that, subjectively, the best image for him is generated. By way of example, he uses the beam shift to show the same sample positions and the contrasts of the detectors to avoid a saturation of the brightness in the images, and the objective current in order to focus the image. By way of example, he sets the following values to this end:

Landing energy=5 keV=$A_1(S2)$

Beam shift $x=28\%=A_2(S2)$

Beam shift $y=-43\%=A_3(S2)$

Lens current in the objective lens=1350 mA=$A_4(S2)$

Stigmator $x=-6\%=A_5(S2)$

Stigmator $y=25\%=A_6(S2)$

Contrast detector 1=32%=$A_7(S2)$

Contrast detector 2=18%=$A_8(S2)$

This set of control parameters $A_i(S2)$, with i=1, 2, . . . 8, for a landing energy of 5 keV is likewise stored, likewise optionally with further control parameters which are not modified.

The user now wishes to examine the landing energy range between 1 kV and 5 kV. He selects the linear interpolation. Now, all required control parameters $A_i$ are calculated in interpolated fashion between the nodes, i.e. the control parameters $A_i(S1)$ and $A_i(S2)$:

$$A_1(s)=A_1(S1)+(A_1(S2)-A_1(S1))s \quad [6]$$

$$A_2(s)=A_2(S1)+(A_2(S2)-A_2(S1))s \quad [7]$$

$$A_3(s)=A_3(S1)+(A_3(S2)-A_3(S1))s \quad [8]$$

$$A_4(s)=A_4(S1)+(A_4(S2)-A_4(S1))s \quad [9]$$

$$A_5(s)=A_5(S1)+(A_5(S2)-A_5(S1))s \quad [10]$$

$$A_6(s)=A_6(S1)+(A_6(S2)-A_6(S1))s \quad [11]$$

$$A_7(s)=A_7(S1)+(A_7(S2)-A_7(S1))s \quad [12]$$

$$A_8(s)=A_8(S1)+(A_8(S2)-A_8(S1))s \quad [13]$$

The user may subsequently set arbitrary values of the landing energy in the aforementioned region or outside of the aforementioned region. From equation 6, the controller of the particle beam apparatus determines the associated value of the parameter s for the set landing energy and, by inserting this parameter s into above equations 7 to 13, at all times determines a calculated prescription for all control parameters $A_2$ to $A_8$, which is accordingly set by the controller of the particle beam apparatus. By way of example, the interpolation or extrapolation of the beam shift always ensures that the same positions on the object may be observed for the entire energy range of 1-5 kV in the depicted image of the object and the detector contrasts are always set in an ideal manner and the image is always approximately focused.

If the image quality does not suffice for the user at a set landing energy, e.g. at a landing energy of 2.3 keV, the user may set a further node at this location. He manually adjusts the set of control parameters for this landing energy and then obtains the following set of control parameters:

Landing energy=2.3 keV=$A_1(S3)$

Beam shift $x=22\%=A_2(S3)$

Beam shift $y=-41\%=A_3(S3)$

Lens current in the objective lens=1123 mA=$A_4(S3)$

Stigmator $x=-8\%=A_5(S3)$

Stigmator $y=20\%=A_6(S3)$

Contrast detector 1=31%=$A_7(S3)$

Contrast detector 2=19.3%=$A_8(S3)$

The following advantages emerge from the above-described procedure:

- As a result of the preceding linear interpolation, the fine adjustment of the control parameters at the new node S3 may, as a rule, be carried out with less adjustment outlay since the preset values of all control parameters already lie in the vicinity of the optimum.
- A further subsequent interpolation is now carried out with three nodes S1, S2 and S3, i.e. the user is now able to select a higher order interpolation method. By way of example, splines may be selected and used for subsequent interpolations.
- The control parameters $A_i$ interpolated by the subsequent interpolation have a higher quality in the local vicinity of the new node S3 and the user obtains a better image quality.

In order to further improve the image quality at certain settings of the landing energy, the user may apply further nodes and use suitable interpolation methods, i.e. carry out interval nesting of the nodes at the landing energy values for example.

The above-described example is not restricted to the manual adjustment of the control parameters at the nodes. The user may likewise run an automated adjustment of the control parameters according to an objective criterion. Then, the underlying algorithm is more robust and faster on account of the aforementioned advantages.

Likewise, after setting the nodes, the user can let the particle beam apparatus record images in a selected energy range, e.g. 1.7 keV<=landing energy<=4.5 keV, with a certain increment, e.g. dLE=0.1 keV, in an automated manner. In the process the required control parameters A are calculated by interpolation in an interpolated manner, for example by virtue of the controller of the particle beam apparatus determining the respectively associated values of the parameter s from equation 6 above for the series of landing energy values emerging from the selected increment and subsequently iteratively inserting the values of the parameters into equations 7 to 13. In this way, 29 sets of control parameters $A_1$ to $A_8$ (including the sets of control parameters at the interval boundaries) emerge for the aforementioned interval of 1.7 keV to 4.5 keV. Then, the particle beam apparatus is subsequently operated with these 29 sets of control parameters being set and an image of the object is in each case recorded for each set of control parameters. By way of example, this may be advantageous if the image recordings take a relatively long time on account of long integration times or if the particle beam apparatus requires a certain amount of time to obtain a certain image stability after a set of new control parameters were set on account of a settling process. After completion of this automatic series of image recordings, the user is then able to look at the stored image stack and, for example, analyze the aforementioned contrasts.

The above-described method is usable not only in particle beam apparatuses with a single particle beam but also in apparatuses in which a multiplicity of primary particle beams are generated simultaneously. In particular, these may be so-called multi-beam particle beam apparatuses, in which a multiplicity of particle beams (e.g. 61 or more than 100) are generated and guided within a common particle optical unit. However, these may also be so-called multi-column apparatuses, which comprise a multiplicity of particle-optical columns arranged in parallel.

Both in the case of individual beam apparatuses and in the case of multi-beam apparatuses, the particles detected for obtaining an image signal may, in particular, be primary particles scattered back at the object or primary particles transmitted through the object.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a non-transitory computer readable medium and executed by one or more processors, including one or more processors of a server or a desktop computer. The system described herein may be used in connection with any appropriate operating system.

The features of the invention disclosed in the present description, in the drawings and in the claims may be essential for the realization of the invention in the various embodiments thereof, both individually and in arbitrary combinations. The invention is not restricted to the described embodiments. It may be varied within the scope of the claims, taking into account the knowledge of the relevant person skilled in the art.

What is claimed is:

1. A method for generating an image of an object and/or a representation of data about the object using a particle beam apparatus, the particle beam apparatus having at least one beam generator for generating a particle beam comprising charged particles, the charged particles have a landing energy when incident on the object, the particle beam apparatus having at least one guide unit for guiding the particle beam onto the object and including at least one control unit for setting the guide unit by selecting a value of a control parameter of the control unit, the particle beam apparatus including at least one detector for detecting interaction particles and/or interaction radiation which emerge/emerges from an interaction between the particle beam and the object when the particle beam is incident on the object, and wherein the particle beam apparatus includes at least one display unit for displaying an image of the object and/or a representation of data about the object, wherein the image and/or the representation is/are generated on the basis of detection signals which are generated by detecting the interaction particles and/or interaction radiation, the method comprising:

setting a landing energy of the charged particles to a first value from a predeterminable range of the landing energy;

setting a first control parameter value of the control parameter, at which a first image of the object with a desired image quality and/or a first desired representation of data about the object is/are obtained;

setting the landing energy to a second value from the predeterminable range of the landing energy;

setting a second control parameter value of the control parameter, at which a second image of the object with a desired image quality and/or a second desired representation of data about the object is/are obtained;

determining a functional relationship between the first control parameter value and the second control parameter value depending on the predeterminable range of the landing energy;

setting a desired value of the landing energy;

selecting the value of the control parameter corresponding to the desired value of the landing energy based on the determined functional relationship; and controlling the guide unit with the value of the control parameter corresponding to the desired value of the landing energy.

2. The method as claimed in claim 1, wherein the particle beam apparatus includes at least one memory unit, further comprising:

storing the first control parameter value and the first value of the landing energy in the memory unit;

storing the second control parameter value and the second value of the landing energy in the memory unit; and reading the first control parameter value, the first value of the landing energy, the second control parameter value and the second value of the landing energy from the memory unit before determining the functional relationship.

3. The method as claimed in claim 2, wherein the functional relationship is stored in the memory unit.

4. The method as claimed in claim 1, wherein the corresponding value of the control parameter is calculated for each value of the predeterminable range of the landing energy by means of the functional relationship, and wherein each value of the predeterminable range of the landing energy and the value of the control parameter corresponding to this value are stored in a memory unit.

5. The method as claimed in claim 4, wherein the corresponding value of the control parameter is read from the memory unit when selecting the value of the control parameter corresponding to the desired value of the landing energy.

6. The method as claimed in claim 1, further comprising:

setting the landing energy to a third value from the predeterminable range of the landing energy;

selecting a third control parameter value of the control parameter, at which a third image of the object with the desired image quality and/or a third desired representation of data about the object is/are obtained; and determining the functional relationship by additionally taking into account the third control parameter value depending on the predeterminable range of the landing energy.

7. The method as claimed in claim 1, wherein the guide unit of the particle beam apparatus is a first guide unit, the control parameter is a first control parameter and the control unit is a first control unit for setting the first guide unit, the particle beam apparatus including at least one second guide unit for guiding the particle beam onto the object and at least one second control unit for setting the second guide unit by selecting a value of a second control parameter of the second control unit, the method further comprising:

setting a first control parameter value of the second control parameter after setting the landing energy to the first value from the predeterminable range of the landing energy, the first image of the object with a desired image quality and/or the first desired representation of data about the object being obtained at said first control parameter value;

setting a second control parameter value of the second control parameter after setting the landing energy to the second value from the predeterminable range of the landing energy, the second image of the object with a desired image quality and/or the second desired representation of data about the object being obtained at said second control parameter value;

determining a further functional relationship between the first control parameter value of the second control parameter and the second control parameter value of the second control parameter depending on the predeterminable range of the landing energy;

selecting the value of the second control parameter corresponding to the desired value of the landing energy based on the determined further functional relationship after setting the landing energy to the desired value of the landing energy from the predeterminable range of the landing energy;

controlling the second guide unit with the value of the second control parameter corresponding to the desired value of the landing energy.

8. The method as claimed in claim 1, wherein the functional relationship is determined by at least one of: interpolation, extrapolation, averaging, ascertaining random numbers, determining a smallest value of the set of the first value and the second value, or determining a largest value of the set of the first value and the second value.

9. The method as claimed in claim 1, wherein the functional relationship is a linear functional relationship or a nonlinear functional relationship.

10. The method as claimed in claim 1, wherein the first control parameter value and/or the second control parameter value is/are used to control at least one of the following units:

at least one objective lens for focusing the particle beam onto the object;
at least one electrostatic and/or magnetic unit;
at least one stigmator; and
at least one mechanically adjustable aperture unit.

11. A computer program product comprising program code, which may be loaded into a processor of a particle beam apparatus having at least one beam generator for generating a particle beam with charged particles, the charged particles have a landing energy when incident on the object, the particle beam apparatus having at least one guide unit for guiding the particle beam onto the object and including at least one control unit for setting the guide unit by selecting a value of a control parameter of the control unit, the particle beam apparatus including at least one detector for detecting interaction particles and/or interaction radiation which emerge/emerges from an interaction between the particle beam and the object when the particle beam is incident on the object, and wherein the particle beam apparatus includes at least one display unit for displaying an image of the object and/or a representation of data about the object, wherein the image and/or the representation is/are generated on the basis of detection signals which are generated by detecting the interaction particles and/or interaction radiation, the code, when executed, controls the particle beam apparatus by causing the following to be performed:

setting a landing energy of the charged particles to a first value from a predeterminable range of the landing energy;

setting a first control parameter value of the control parameter, at which a first image of the object with a desired image quality and/or a first desired representation of data about the object is/are obtained;

setting the landing energy to a second value from the predeterminable range of the landing energy;

setting a second control parameter value of the control parameter, at which a second image of the object with a desired image quality and/or a second desired representation of data about the object is/are obtained;

determining a functional relationship between the first control parameter value and the second control parameter value depending on the predeterminable range of the landing energy;

setting a desired value of the landing energy;

selecting the value of the control parameter corresponding to the desired value of the landing energy based on the determined functional relationship; and controlling the guide unit with the value of the control parameter corresponding to the desired value of the landing energy.

12. A particle beam apparatus for generating an image of an object and/or a representation of data about the object, comprising:

at least one beam generator for generating a particle beam comprising charged particles, wherein the charged particles have a landing energy when incident on the object;

at least one object holder designed in a movable fashion for holding and positioning the object;

at least one guide unit for guiding the particle beam onto the object;

at least one detector for detecting interaction particles and/or interaction radiation which emerge/emerges from an interaction between the particle beam and the object when the particle beam is incident on the object;

at least one control unit for setting the guide unit by selecting a value of a control parameter of the control unit;

at least one display unit for displaying an image of the object and/or a representation of data about the object, wherein the image and/or the representation is/are generated based on detection signals which are generated by detecting the interaction particles and/or interaction radiation; and at least one processor, onto which a computer program product is loaded, the computer program product containing code that, when executed, controls the particle beam apparatus by causing the following to be performed:

setting a landing energy of the charged particles to a first value from a predeterminable range of the landing energy;

setting a first control parameter value of the control parameter, at which a first image of the object with a desired image quality and/or a first desired representation of data about the object is/are obtained;

setting the landing energy to a second value from the predeterminable range of the landing energy;

setting a second control parameter value of the control parameter, at which a second image of the object with a desired image quality and/or a second desired representation of data about the object is/are obtained;

determining a functional relationship between the first control parameter value and the second control parameter value depending on the predeterminable range of the landing energy;

setting a desired value of the landing energy;

selecting the value of the control parameter corresponding to the desired value of the landing energy based on the determined functional relationship; and controlling the guide unit with the value of the control parameter corresponding to the desired value of the landing energy.

13. The particle beam apparatus as claimed in claim 12, wherein the guide unit comprises at least one of the following features:
- at least one objective lens for focusing the particle beam onto the object;
- at least one electrostatic and/or magnetic unit;
- at least one stigmator;
- at least one condenser lens; and
- at least one mechanically adjustable aperture unit.

14. The particle beam apparatus as claimed in claim 12, wherein the beam generator is embodied as a first beam generator and the particle beam is embodied as a first particle beam comprising first charged particles, wherein the guide unit is embodied as a first guide unit for guiding the first particle beam onto the object, and wherein the particle beam apparatus furthermore includes at least one second beam generator for generating a second particle beam comprising second charged particles and at least one second guide unit for guiding the second particle beam onto the object.

15. The particle beam apparatus as claimed in claim 12, wherein the particle beam apparatus is an electron beam apparatus and/or an ion beam apparatus.

* * * * *

UNITED STATES PATENT AND TRADEMARK OFFICE
CERTIFICATE OF CORRECTION

PATENT NO. : 10,274,441 B2  
APPLICATION NO. : 15/600910  
DATED : April 30, 2019  
INVENTOR(S) : Christian Hendrich Page 1 of 1

It is certified that error appears in the above-identified patent and that said Letters Patent is hereby corrected as shown below:

In the Specification

Column 22, Line 47, please replace "angle of 90°.Hence," with -- angle of 90°. Hence, --

Column 38, Line 61, please replace "A" with -- $A_i$ --

Column 39, Line 1, please replace "parameters" with -- parameter s --

Signed and Sealed this  
Twentieth Day of August, 2019

Andrei Iancu  
*Director of the United States Patent and Trademark Office*